United States Patent
Harris et al.

(10) Patent No.: US 12,108,941 B2
(45) Date of Patent: Oct. 8, 2024

(54) TUBING ASSEMBLIES AND METHODS FOR FLUID DELIVERY

(71) Applicant: Boston Scientific Scimed, Inc., Maple Grove, MN (US)

(72) Inventors: Colby Harris, Norfolk, MA (US); Ryan Pollock, Leominster, MA (US); Ryan Wales, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 207 days.

(21) Appl. No.: 17/558,256

(22) Filed: Dec. 21, 2021

(65) Prior Publication Data

US 2022/0192479 A1    Jun. 23, 2022

Related U.S. Application Data

(60) Provisional application No. 63/129,204, filed on Dec. 22, 2020, provisional application No. 63/129,199, filed on Dec. 22, 2020.

(51) Int. Cl.
*A61B 1/00*       (2006.01)
*A61B 1/015*      (2006.01)
(Continued)

(52) U.S. Cl.
CPC .......... *A61B 1/126* (2013.01); *A61B 1/00119* (2013.01); *A61B 1/00137* (2013.01);
(Continued)

(58) Field of Classification Search
CPC . A61B 1/126; A61B 1/00119; A61B 1/00137; A61B 1/015; B08B 3/04; B08B 5/02
(Continued)

(56) References Cited

U.S. PATENT DOCUMENTS 4,552,130 A      11/1985  Kinoshita
2010/0256448 A1  10/2010  Smith et al.
(Continued)

OTHER PUBLICATIONS

International Search Report and Written Opinion dated Mar. 22, 2022 for International Application No. PCT/US2021/064695.

*Primary Examiner* — Timothy J Neal
*Assistant Examiner* — James Edward Boice
(74) *Attorney, Agent, or Firm* — Seager, Tufte & Wickhem, LLP

(57) ABSTRACT

This disclosure relates generally to medical tubing assemblies and methods for fluid delivery from a single fluid reservoir. In one example, a tubing assembly may be configured to couple to an endoscope for distributing fluid between the endoscope and a fluid reservoir during an endoscopic procedure. The assembly may comprise a tubing manifold, a cap configured to be removably attached to the fluid reservoir, a portion of gas supply tubing and lens wash supply tubing in fluid communication between the manifold and the endoscope, a portion of gas supply tubing in fluid communication between the cap and the manifold, and a portion of lens wash supply tubing in fluid communication between the fluid reservoir and the manifold. Further examples may include portions of irrigation supply tubing and portions of alternate gas supply tubing selectively connectable in fluid communication between the manifold, fluid reservoir and endoscope.

12 Claims, 21 Drawing Sheets

(51) Int. Cl.
  *A61B 1/12*   (2006.01)
  *B08B 3/04*   (2006.01)
  *B08B 5/02*   (2006.01)
(52) U.S. Cl.
  CPC ................ *A61B 1/015* (2013.01); *B08B 3/04* (2013.01); *B08B 5/02* (2013.01)
(58) Field of Classification Search
  USPC ........................................................ 600/157
  See application file for complete search history.

(56) References Cited

U.S. PATENT DOCUMENTS

| | | | |
|---|---|---|---|
| 2010/0318059 A1* | 12/2010 | Farritor | A61B 1/00188 604/82 |
| 2014/0309496 A1 | 10/2014 | Bendele et al. | |
| 2015/0374213 A1 | 12/2015 | Maurice, Jr. | |
| 2016/0243329 A1* | 8/2016 | Chen | A61M 16/1005 |
| 2017/0296046 A1* | 10/2017 | King | B08B 9/0321 |

* cited by examiner

TUBING ASSEMBLIES AND METHODS FOR FLUID DELIVERY

RELATED APPLICATIONS

This application claims the benefit of priority under 35 U.S.C. § 119 to U.S. Provisional Patent Application No. 63/129,204, titled "Integrated Container and Tube Set for Fluid Delivery with an Endoscope", filed on Dec. 22, 2020, the entirety of which is incorporated herein by reference.

This application claims the benefit of priority under 35 U.S.C. § 119 to U.S. Provisional Patent Application No. 63/129,199, titled "Tubing Assemblies and Methods for Fluid Delivery", filed on Dec. 22, 2020, the entirety of which is incorporated herein by reference.

FIELD

This disclosure relates generally to medical tubing assemblies and methods for fluid delivery, and particularly tubing assemblies for an endoscope with fluid delivery from a single water source.

BACKGROUND

Conventionally, endoscope devices have been widely used. An endoscope performs diagnostic and/or therapeutic treatment by inserting the elongated shaft of the endoscope into the subject to observe the part to be examined within the body cavity and, if necessary, inserting a treatment instrument/tool into the working channel of the endoscope.

Such endoscope devices include a fluid/lens wash capability, or the like, configured to feed fluid such as gas (e.g., air, $CO_2$) to the end of the endoscope for insufflating the inside of the patient at the target site. Lens wash provides sterilized water at relatively high pressure to spray across and clear the camera lens of debris. In order to rinse the target site of the subject, separate from the air/water feed capability, endoscope devices have an irrigation capability that provides lower pressure, higher volume water, supplied via a pump (e.g., peristaltic pump) to the target site in order to clear the field of view for observation and treatment. The water source for lens wash and irrigation typically has included one or more fluid reservoirs having tubing and cap assemblies that create a plumbing circuit in connection with the endoscope channels and valving to accomplish the gas and water functions described.

Such tubing and cap assemblies are available in various configurations, which typically involve a water bottle, a cap fitted for the specific bottle, and an array of tubing that is extendable through openings in the cap. The tubing typically is arranged to accommodate a specific configuration of endoscope fittings and valving, which does not tend to be modular or optional.

It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

According to an aspect, a tubing assembly may be arranged and configured to couple to an endoscope for distributing fluid between the endoscope and a fluid reservoir during an endoscopic procedure. The assembly may comprise a tubing manifold, a cap, gas supply tubing, and lens wash tubing. The cap may be configured to be removably attached to the fluid reservoir, a portion of the gas supply tubing may be configured for connection in fluid communication between the manifold and the endoscope, a portion of the lens wash supply tubing may be configured for connection in fluid communication between the manifold and the endoscope, a portion of gas supply tubing may be configured for connection in fluid communication between the cap and the manifold, and a portion of lens wash supply tubing may be configured for connection in fluid communication between the fluid reservoir and the manifold.

In various embodiments, the assembly may further comprise irrigation supply tubing. A portion of the irrigation supply tubing may be configured for connection in fluid communication between the endoscope and the manifold, a portion may be configured for connection between the manifold and the fluid reservoir, or both. In various embodiments, the portion of lens wash supply tubing and the portion of irrigation supply tubing between the fluid reservoir and the manifold may be the same portion of tubing. In various embodiments, a flow of liquid from the fluid reservoir to the manifold through the same portion of lens wash supply tubing and irrigation supply tubing may be deliverable to the endoscope for irrigation use, lens wash use, or both. In various embodiments, the same portion of lens wash supply tubing and irrigation supply tubing, between the manifold and the fluid reservoir, may be arranged coaxially within the portion of gas supply tubing between the manifold and the cap. In various embodiments, the portion of lens wash supply tubing between the endoscope and the manifold may be arranged coaxially within the portion of gas supply tubing between the endoscope and the manifold. In various embodiments, the assembly may further comprise a split flow adapter. The adapter on one end may be operatively coupled to the coaxially arranged portions of lens wash supply tubing and gas supply tubing between the endoscope and manifold. The adapter on an opposite end may be configured to interface with a side-by-side connection to the endoscope. In various embodiments, the assembly may further comprise an alternate gas supply tubing. A portion of the alternate gas supply tubing may be configured for connection in fluid communication between an alternate gas source and the manifold, a portion may be configured for connection between the manifold and the cap, a portion may be configured for connection between the manifold and the endoscope, or combinations thereof. In various embodiments, the portions of gas supply tubing and alternate gas supply tubing, between the manifold and the endoscope may be the same portion of tubing, and the portions of gas supply tubing and alternate gas supply tubing between the manifold and the cap may be the same portion of tubing. In various embodiments, a directional flow of gas from the alternate gas source between the manifold and the endoscope may be opposite a directional flow of gas from the endoscope to the manifold. In various embodiments, the portion of irrigation supply tubing between the manifold and the endoscope, the portion of alternate gas supply tubing between the manifold and the alternate gas source, or both, may be configured to be selectively connectable to the manifold. Each selectively connectable portion of tubing may further comprise a penetrating member disposed on a respective manifold end thereof. In various embodiments, the assembly may further comprise an irrigation supply opening and an alternate gas supply opening arranged on the manifold. Each of the openings may further comprise a breakable seal puncturable by the respective penetrating member of the corresponding portion of irrigation supply tubing or alternate gas supply tubing when selected to be connectable thereto. In various embodiments, the portion of irrigation supply tubing, the portion of lens wash supply tubing, or the portion of gas supply tubing, or combinations thereof, between the endoscope and manifold, may be connectible with a one-way valve. In various embodiments, the portion of irrigation supply tubing between the manifold and the endoscope, the portion of alternate gas supply tubing between the manifold and the alternate gas source, or both, may be fixed to the manifold and may include an adjustable fitting coupled thereto. The adjustable fitting may be moveable between a closed position and an opened position.

According to a further aspect, a tubing system may be arranged and configured for distributing fluid during an endoscopic procedure. The system may comprise an endoscope, a fluid reservoir, and a tubing assembly. The tubing assembly may comprise a tubing manifold, gas supply tubing and lens wash tubing. A portion of the gas supply tubing and a portion of the lens wash supply tubing may be connected in fluid communication between the manifold and the endoscope. A portion of the gas supply tubing and a portion of the lens wash supply tubing may be connected in fluid communication between the fluid reservoir and the manifold.

In various embodiments, the system may further comprise irrigation supply tubing. A portion of the irrigation supply tubing may be connected in fluid communication between the endoscope and the manifold, a portion may be connected between the manifold and the fluid reservoir, or both. In various embodiments, the portion of lens wash supply tubing and the portion of irrigation supply tubing between the fluid reservoir and the manifold may be the same portion of tubing. In various embodiments, the system may further comprise alternate gas supply tubing. A portion of the alternate gas supply tubing may be connected in fluid communication between an alternate gas source and the manifold, a portion may be connected between the manifold and the fluid reservoir, a portion may be connected between the manifold and the endoscope, or combinations thereof. In various embodiments, the portion of irrigation supply tubing between the manifold and the endoscope, the portion of alternate gas supply tubing between the manifold and the alternate gas source, or both, may be configured to be selectively connectable to the manifold. Each selectively connectable portion of tubing may further comprise a penetrating member disposed on a respective manifold end of the tubing. In various embodiments, the system may further comprise an irrigation supply opening and an alternate gas supply opening arranged on the manifold. Each of the openings may comprise a breakable seal puncturable by the respective penetrating member of the corresponding portion of irrigation supply tubing or alternate gas supply tubing when selected to be connectable thereto.

According to a further aspect, a modular tubing assembly manifold may be arranged and configured for distributing fluid between a fluid reservoir and an endoscope. The manifold may comprise a portion of gas supply tubing and a portion of lens wash supply tubing connectable in fluid communication between the manifold and the endoscope. The manifold may comprise a portion of gas supply tubing and a portion of lens wash supply tubing connectable in fluid communication between the fluid reservoir and the manifold.

In various embodiments, the manifold may further comprise a portion of irrigation supply tubing selectively connectible in fluid communication between the endoscope and the manifold, a portion of irrigation supply tubing selectively connectible between the manifold and the fluid reservoir, or both. In various embodiments, the portions of lens wash supply tubing and irrigation supply tubing between the fluid reservoir and the manifold may be the same portion of tubing. In various embodiments, the manifold may further comprise a portion of alternate gas supply tubing selectively connectible in fluid communication between an alternate gas source and the manifold, a portion of alternate gas supply tubing selectively connectible between the manifold and the fluid reservoir, a portion of alternate gas supply tubing selectively connectible between the manifold and the endoscope, or combinations thereof. In various embodiments, the portion of irrigation supply tubing between the manifold and the endoscope, the portion of alternate gas supply tubing between the manifold and the alternate gas source, or both, may further comprise a penetrating member disposed on a respective manifold end thereof. In various embodiments, the manifold may further comprise an irrigation supply opening and/or an alternate gas supply opening arranged on the manifold. Each of the openings may comprise a breakable seal puncturable by the respective penetrating member of the corresponding portion of irrigation supply tubing or alternate gas supply tubing when selected to be connectable thereto.

According to another aspect, a tubing method for distributing fluid during an endoscopic procedure is disclosed. The method may comprise connecting a portion of gas supply tubing and a portion of lens wash supply tubing in fluid communication between an endoscope and a tubing manifold, connecting a portion of gas supply tubing and a portion of lens wash supply tubing in fluid communication between the tubing manifold and a fluid reservoir, supplying gas to the fluid reservoir through the portions of gas supply tubing between the endoscope and the manifold and between the manifold and the fluid reservoir, and supplying lens wash liquid from the fluid reservoir through the portions of lens wash supply tubing between the fluid reservoir and the manifold and between the manifold and the endoscope.

In various embodiments, the method may further comprise connecting a portion of irrigation supply tubing connected in fluid communication between the endoscope and the manifold, a portion of irrigation supply tubing connected between the manifold and the fluid reservoir, or both. In various embodiments, the portions of lens wash supply tubing and irrigation supply tubing between the fluid reservoir and the manifold may be the same portion of tubing. In various embodiments, the method may further comprise supplying a flow of liquid from the fluid reservoir to the manifold for irrigation use, lens wash use, or both, through the same portion of lens wash supply tubing and irrigation supply tubing. In various embodiments, the method may further comprise connecting a portion of alternate gas supply tubing connected in fluid communication between an alternate gas source and the manifold, a portion of alternate gas supply tubing connected between the manifold and the fluid reservoir, a portion of alternate gas supply tubing connected between the manifold and the endoscope, or combinations thereof.

According to another aspect, a tubing assembly may be arranged and configured to couple to an endoscope for distributing fluid between the endoscope and a fluid reservoir during an endoscopic procedure. The assembly may comprise a fluid manifold and a gas/lens wash connection. The fluid manifold may include a coaxial tubing port, a gas umbilicus port, a lens wash umbilicus port, and an irrigation supply port. The coaxial tubing port may be in fluid communication with the gas umbilicus port, the lens wash umbilicus port, and the irrigation supply port. The gas/lens wash connection may be coupled to the fluid manifold and be configured to interface with an endoscope. The gas/lens connection may include a lens wash connector and a gas connector. The lens wash connector may include a first opening in fluid communication with the lens wash umbilicus port and the gas connector may include a second opening in fluid communication with the gas umbilicus port.

Some embodiments include a coaxial tube coupled to the coaxial tubing port, the coaxial tube comprising an inner tube and an outer tube. In some such embodiments, a lumen of the outer tube is in fluid communication with the gas umbilicus port and a lumen of the inner tube is in fluid communication with the lens wash umbilicus port and the irrigation supply port. In various such embodiments, the outer tube extends around an exterior portion of the fluid manifold and the inner tube extends into an interior portion of the fluid manifold. In many embodiments, the gas/lens wash connection comprises a polymer and the fluid manifold comprises a metal. In several embodiments, the gas/lens wash connection comprises an opening surrounding the irrigation supply port. In some embodiments, the fluid manifold includes an alternative gas supply port in fluid communication with the gas umbilicus port and the coaxial tubing port.

According to another aspect, a tubing assembly may be arranged and configured to couple to an endoscope for distributing fluid between the endoscope and a fluid reservoir during an endoscopic procedure. The assembly may comprise a split manifold, a first coaxial tube, and a second coaxial tube. The split manifold may include a first coaxial tubing port, a second coaxial tubing port, an irrigation supply port, and an alternative gas supply port. The first coaxial tube may be coupled to the first coaxial tubing port and include a first inner tube and a first outer tube. The second coaxial tube may be coupled to the second coaxial tubing port and include a second inner tube and a second outer tube. The first inner tube may be in fluid communication with the irrigation supply port and the second inner tube and the first outer tube may be in fluid communication with the alternative gas supply port and the second outer tube.

In some embodiments, the first outer tube surrounds the first coaxial tubing port and the second out tube surrounds the second coaxial tubing port. In various embodiments, the first coaxial tubing port includes a first liquid port and a first gas port, the second coaxial tubing port includes a second liquid port and a second gas port. In various such embodiments, one or more of the first gas port and the second gas port includes a crescent shaped opening. In several such embodiments, the first inner tube extends into the first liquid port and the second inner tube extends into the second liquid port. In further such embodiments, the first outer tube may surround the first liquid port and the first gas port and the second outer tube surrounds the second liquid port and the second gas port. In many embodiments, the irrigation supply port extends from the split manifold with an obtuse angle with respect to the second coaxial port.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

DETAILED DESCRIPTION

Figure 1:
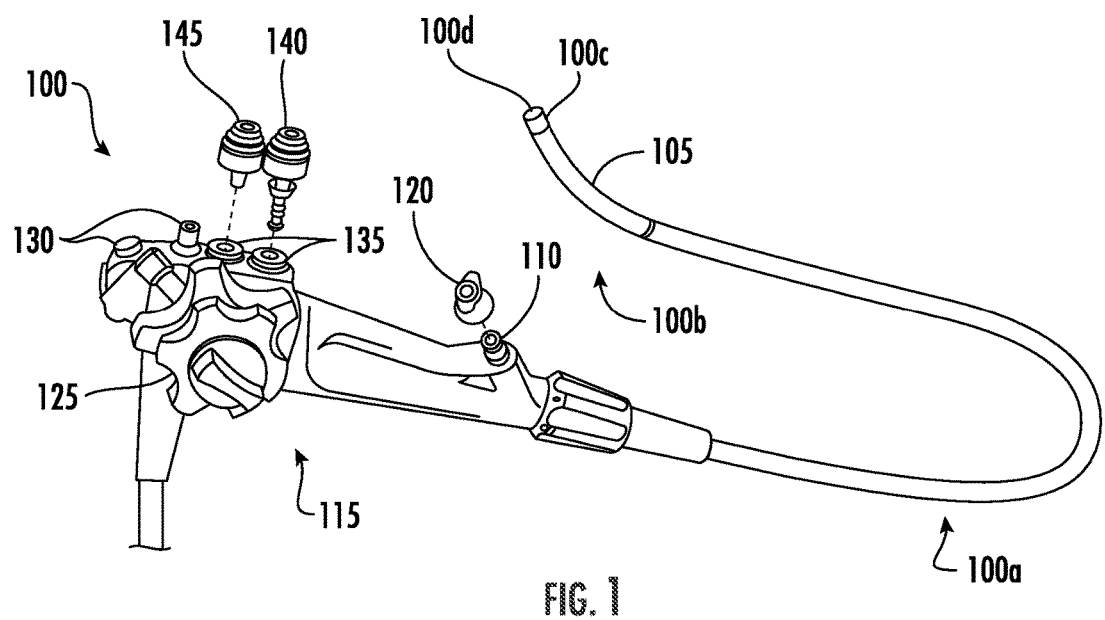
FIG. 1 illustrates components of an endoscope.

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts under lying the disclosed devices and related methods of use may be utilized in any suitable procedure, medical or otherwise. This disclosure may be understood with reference to the following description and the appended drawings, wherein like elements are referred to with the same reference numerals.

Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Although embodiments of the present disclosure are described with specific reference to a tubing assembly for use in distributing liquid from a reservoir (e.g., container, bottle, or the like) and one or more gases from different sources, it should be appreciated that such embodiments may be used to supply liquid and/or gas to and/or from an endoscope, for a variety of different purposes, including, for example to facilitate insufflation of a patient, lens washing, and/or to irrigate the working end of an endoscope in a patient to aid in flushing/rinsing the body lumen and/or to clear debris from the field of view of the endoscope in the body lumen, during an endoscopic procedure. Use of "lens wash" refers to liquid (e.g., water) being flowed, typically at a higher flow rate and pressure compared to irrigation, to a nozzle or other opening at a distal end of an endoscope for the purpose of washing or otherwise clearing or cleaning the lens covering an imaging or light source at the distal end of the endoscope.

Although the present disclosure includes description of a bottle and tube set (e.g., a tubing assembly) suitable for use with an endoscope system to supply fluids to an endoscope, the devices, systems, and methods herein could be implemented in other medical systems requiring fluid delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Exemplary features (e.g., configurations and materials for fluid reservoirs, valving, fittings, etc.), with which embodiments of the present disclosure may be implemented include, but are not limited to, those described in U.S. patent application Ser. No. 17/558,239, titled "Integrated Container and Tube Set for Fluid Delivery with an Endoscope," filed even date herewith, the complete disclosure of which is incorporated by reference herein in its entirety.

Figure 2:
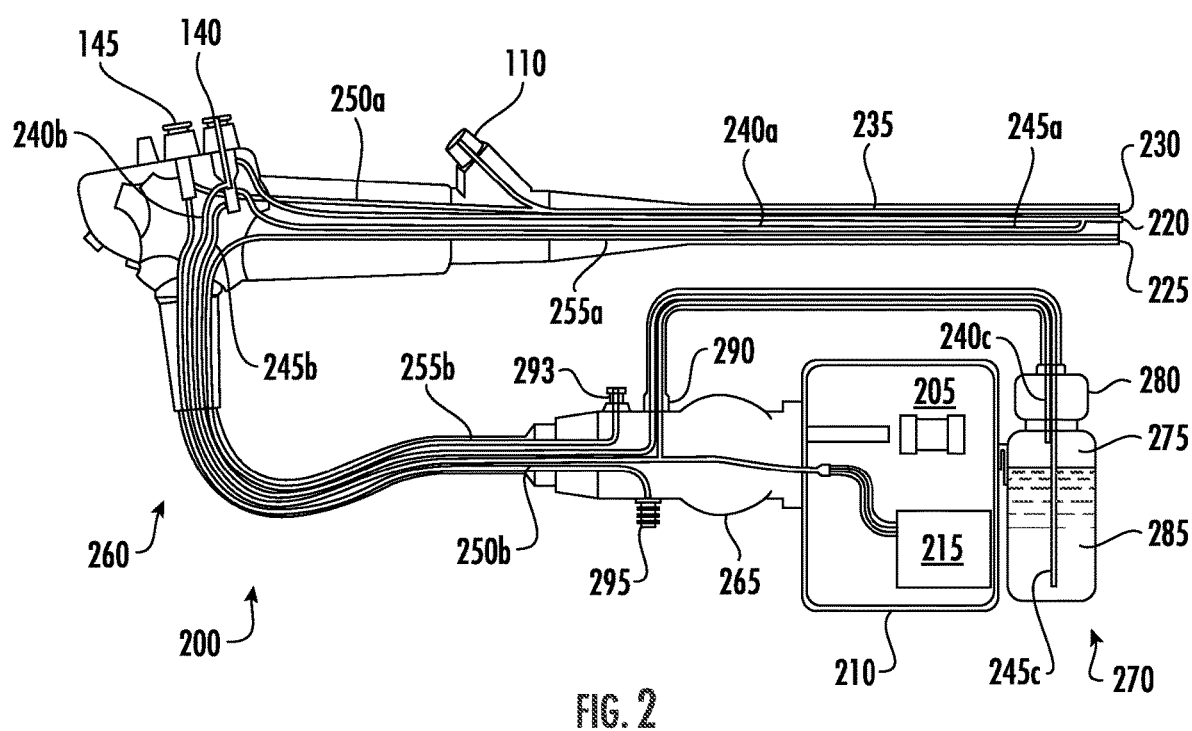
FIG. 2 illustrates components of an endoscope system with endoscope, light source, light source connector, water reservoir, and tubing assembly for air and lens wash fluid delivery.

With reference to FIGS. 1-2, an exemplary endoscope 100 and system 200 is depicted that may comprise an elongated shaft 100a that is insertable into a patient. A light source 205 feeds illumination light to a distal portion 100b of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100a may include a distal tip 100c provided at the distal portion 100b of the shaft 100a and a flexible bending portion 105 proximal to the distal tip 100c. The flexible bending portion 105 may include an articulation joint (not shown) to assist with steering the distal tip 100c. On an end face 100d of the distal tip of the endoscope 100 is a gas/lens wash nozzle 220 for supplying gas to insufflate the interior of the patient at the treatment area and for supplying water to wash a lens covering the imager. An irrigation opening 225 in the end face 100d supplies irrigation fluid to the treatment area of the patient. Illumination windows (not shown) that convey illumination light to the treatment area, and an opening 230 to a working channel 235 extending along the shaft 100a for passing tools to the treatment area, also may be included on the face 100d of the distal tip 100c. The working channel 235 extends along the shaft 100a to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle is provided with dual valve wells 135 that receive a gas/lens wash valve 140 for operating an insufflating gas and lens water feed operation. A gas supply line 240a and a lens wash (e.g., liquid) supply line 245a run distally from the gas/water valve 140 along the shaft 100a and converge at the distal tip 100c proximal to the gas/wash nozzle 220 (FIG. 2). The other valve well 135 receives a suction valve 145 for operating a suction operation. A suction supply line 250a runs distally from the suction valve 145 along the shaft 100a to a junction point in fluid communication with the working channel 235 of the endoscope 100.

The operating handle 115 is electrically and fluidly connected to the video processing unit 210, via a flexible umbilicus 260 and connector portion 265 extending therebetween. The flexible umbilicus 260 has a gas (e.g., air or $CO_2$) feed line 240b, a lens wash feed line 245b, a suction feed line 250b, an irrigation feed line 255b, a light guide (not shown), and an electrical signal cable. The connector portion 265 when plugged into the video processing unit 210 connects the light source 205 in the video processing unit with the light guide. The light guide runs along the umbilicus 260 and the length of the endoscope shaft 100a to transmit light to the distal tip 100c of the endoscope 100. The connector portion 265 when plugged into the video processing unit 210 also connects the air pump 215 to the gas feed line 240b in the umbilicus 260.

A fluid reservoir 270 (e.g., water bottle) is fluidly connected to the endoscope 100 through the connector portion 265 and the umbilical 260. A portion of gas supply tubing 240c passes from one end positioned in an air gap 275 between the top 280 (e.g., bottle cap) of the reservoir 270 and the remaining water 285 in the reservoir to a detachable gas/lens wash connection 290 on the outside of the connector portion 265. The gas feed line 240b from the umbilicus 260 branches in the connector portion 265 to fluidly communicate with the gas supply tubing 240c at the detachable gas/lens wash connection 290, as well as the air pump 215. A portion of lens wash tubing 245c, with one end positioned at the bottom of the reservoir 270, passes through the top 280 of the reservoir to the same detachable connection 290 as the gas supply tubing 240c on the connector portion 265. In other embodiments, the connections may be separate and/or separated from each other. The connector portion 265 also has a detachable irrigation connection 293 for irrigation supply tubing (not shown) running from a source of irrigation fluid (not shown) to the irrigation feed line 255b in the umbilicus 260. In some embodiments, irrigation water is supplied via a pump (e.g., peristaltic pump) from a water source independent (not shown) from the water reservoir 270. In other embodiments, the irrigation supply tubing and lens wash tubing 245c may source water from the same fluid reservoir. The connector portion 265 may also include a detachable suction connection 291 for suction feed line 250b and suction supply line 250a fluidly connecting a vacuum source (e.g., hospital house suction) (not shown) to the umbilicus 260 and endoscope 100.

The gas feed line 240b and lens wash feed line 245b are fluidly connected to the valve well 135 for the gas/water valve 140 and configured such that operation of the gas/water valve in the well controls supply of gas or lens wash to the distal tip 100c of the endoscope 100. The suction feed line 250b is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connection portion 265 and branched to the gas/water valve 140 on the operating handle 115 through the gas feed line 240b in the umbilicus 260, as well as through the gas supply tubing 240c to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240a and out the distal tip 100c of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245c, through the connector portion 265, umbilicus 260, through the gas/water valve 140 and down the lens wash supply line 245a, converging with the gas supply line 240a prior to exiting the distal tip 100c of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245c, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240c to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate compared to lens wash is typically required for irrigation water, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump 255c is connected to the irrigation feed line 255b in the umbilicus 260 and the irrigation supply line 255a of endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255b in the umbilicus, and down the irrigation supply line in the shaft 100a of the endoscope to the distal tip 100c. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245c, may be placed in the path of the irrigation supply tubing to help prevent backflow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. The hybrid system 300 includes the single water reservoir 305, a cap 310 for the reservoir, gas supply tubing 240c, lens wash supply tubing 245c, irrigation pump 315 with foot switch 318, upstream irrigation tubing 320 and downstream irrigation supply tubing 255c. The cap 310 may be configured to attach in a seal-tight manner to the water reservoir 305 by a typically threaded arrangement. The cap may include a gasket to seal the cap 310 to the reservoir 305. The gasket can be an O-ring, flange, collar, and/or the like and can be formed of any suitable material. A number of through-openings (325a, 325b, 325c) in the cap 310 are provided to receive, respectively, the gas supply tubing 240c, lens wash supply tubing 245c, and upstream irrigation supply tubing 320. In FIGS. 3A-3D, the system depicted includes separate tubing for gas supply, lens wash and irrigation.

In other embodiments, the gas supply tubing 240c and lens wash tubing 245c may be combined in a coaxial arrangement. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240c, 245c as configured in the fitting 700 of FIGS. 7A-7B). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion 265 (e.g., FIG. 2). An example of a suitable fitting for such transition is depicted as fitting 700 in FIGS. 7A-7B.

In various embodiments, different configurations of valving (not shown) may be incorporated into the tubing of the system 200, 300. For example, an in-flow check valve can be disposed in the path of the gas supply tubing 240c to help prevent backflow into the air pump 215. In this manner, pressure building within the water reservoir 270, 305 creates a pressure difference between the water source and the gas supply tubing 240c helping to maintain a positive pressure in the water source even when large amounts of water may be removed from the water source during the irrigation function. This arrangement compensates for any time lag in air being delivered from the air pump 215 to the water reservoir 270, 305, which might otherwise cause a negative pressure vacuum in the water reservoir. Similarly, an outflow check valve, such as the one-way valve 900 with inlet/outlets 905a, 905b and valve insert 910 of FIG. 9, may be incorporated in the lens wash supply tubing 240c, upstream irrigation supply tubing 320, and/or downstream irrigation supply tubing 255c to help prevent backflow of water from either or both of the lens wash and irrigation tubing in the event of a negative pressure situation, as described.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 270, 305, the pressure in the system may be controlled to maintain the lens wash supply tubing 240c at substantially the pressure necessary to accomplish a lower flow rate lens wash, while compensating for reduced pressure in the water reservoir 270, 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240c.

Figure 3A:
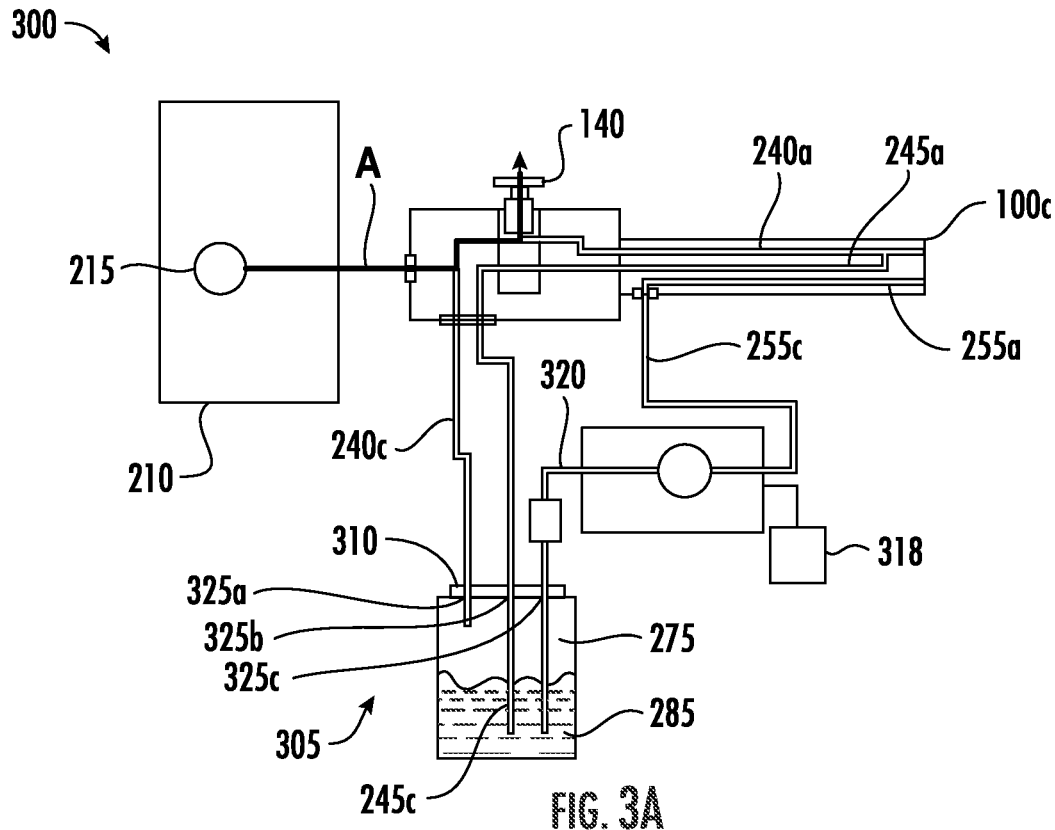
FIG. 3A illustrates an endoscope system with endoscope, light source, water reservoir, and tubing assembly for hybrid air, lens wash and irrigation fluid delivery, wherein the system is activated to deliver air to atmosphere.

The schematic set-up in FIGS. 3A-3D has been highlighted to show the different flow paths possible with the hybrid system 300 having supply tubing for irrigation 320 and lens wash 240c connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240b in the umbilicus 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 240c.

Figure 3B:
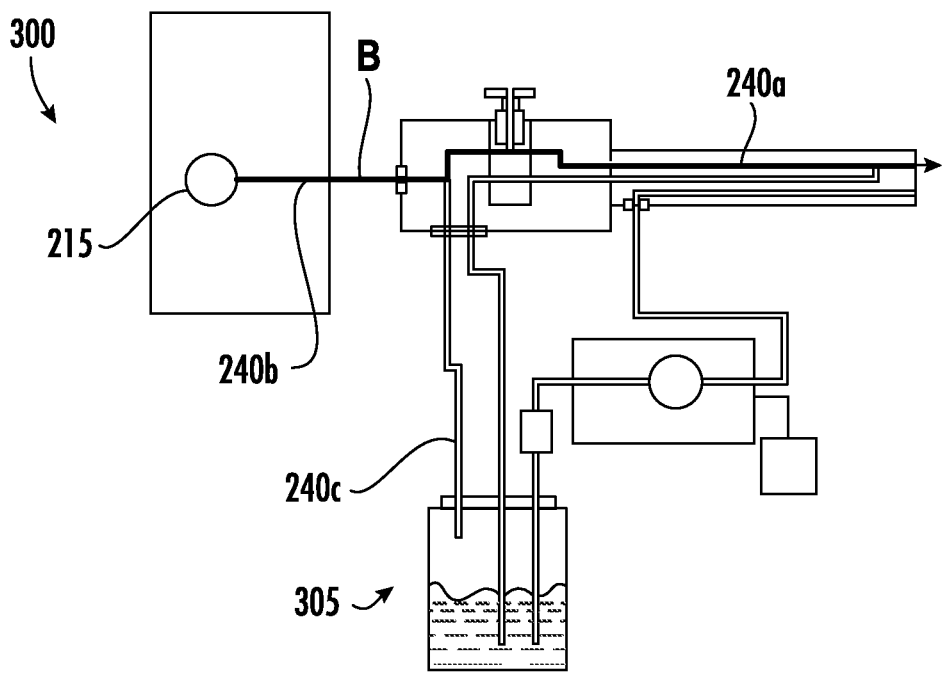
FIG. 3B illustrates the endoscope system of FIG. 3A, wherein the system is activated to deliver air to a patient through the patient end of the endoscope.

As shown in FIG. 3B, the endoscope 100 is in a gas delivery state with the gas/water valve 140 in a first position. When gas is called for at the distal tip 100c, for example, to clean the end face 100d of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240b in the umbilical 260 via the connector portion 265. The gas continues through the gas/water valve 140 to the gas supply line 240a in the endoscope shaft 100a and out the gas/lens wash nozzle 220 at the distal tip 100c. There is no build up to pressurize the water reservoir since the system is open at the gas/lens wash nozzle 220, and consequently no liquid is pushed through the lens wash supply tubing 240c.

Figure 3C:
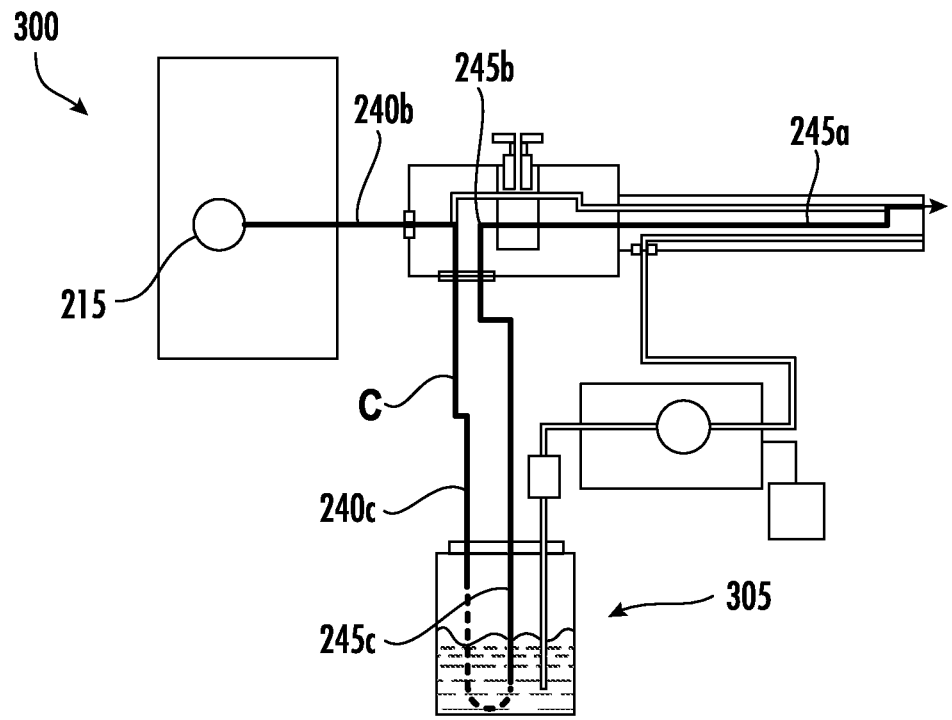
FIG. 3C illustrates the endoscope system of FIG. 3A, wherein the system is activated to deliver lens wash fluid through the patient end of the endoscope.

As shown in FIG. 3C, the endoscope 100 is in a lens wash delivery state with the gas/water valve 140 in a second position. When lens wash is called for at the distal tip 100c, for example, to clean the end face 100d of the distal tip 100c, the user, keeping the vent hole in the air/water valve closed off, depresses the valve 140 to its furthest point in the valve well 135. The second position blocks off the gas supply to both atmosphere and the gas supply line 240a in the endoscope, and opens up the gas/water valve 140 to allow lens wash water to pass through to the lens wash supply line 245a in the endoscope shaft 100a and out the gas/lens wash nozzle 220 at the distal tip 100c. In this state, gas (pressure) is delivered along path C from the air pump 215, through the branched line in the connector portion 265 and out of the gas supply tubing 240c to the water reservoir 305. The gas (pressure) pressurizes the surface of the remaining water 285 in the reservoir 305 and pushes water up the lens wash supply tube 245c to the connector portion 265. The pressurized lens wash water is pushed further through the lens wash feed line 245b in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

Figure 3D:
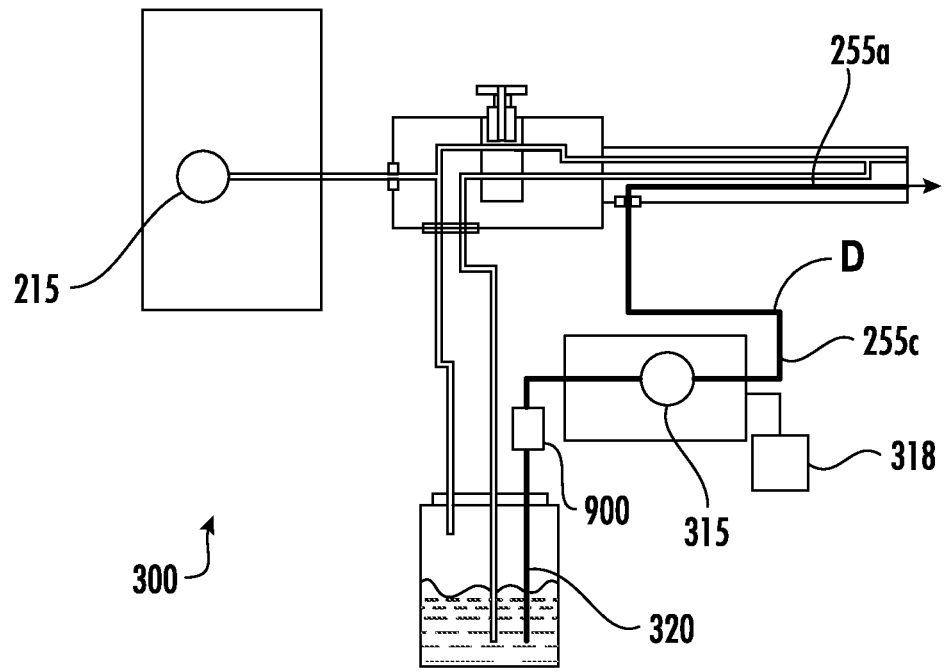
FIG. 3D illustrates the endoscope system of FIG. 3A, wherein the system is activated to deliver irrigation fluid through the patient end of the endoscope.

As shown in FIG. 3D, the endoscope 100 is in an irrigation delivery state. This may be performed at the same or a different time from the delivery of gas and/or lens wash. When irrigation is called for at the distal tip 100c, for example, if visibility in the treatment area is poor or blocked by debris, or the like, the user activates the irrigation pump 315 (e.g., by depressing foot switch 318) to delivery water along path D. With the pump 315 activated, water is sucked out of the water reservoir 305 through the upstream irrigation supply tubing 320 and pumped along the downstream irrigation supply tubing 255c to the connector portion 265. The irrigation pump head pressure pushes the irrigation water further through the irrigation feed line 255b in the umbilical 260, through the irrigation supply line 255a in the endoscope shaft 100a, and out the irrigation opening 225 at the distal tip 100c. The irrigation pump pressure may be calibrated, along with the endoscope irrigation feed and supply lines and external tubing, to deliver a certain range of flow rate of the irrigation fluid.

Figure 4:
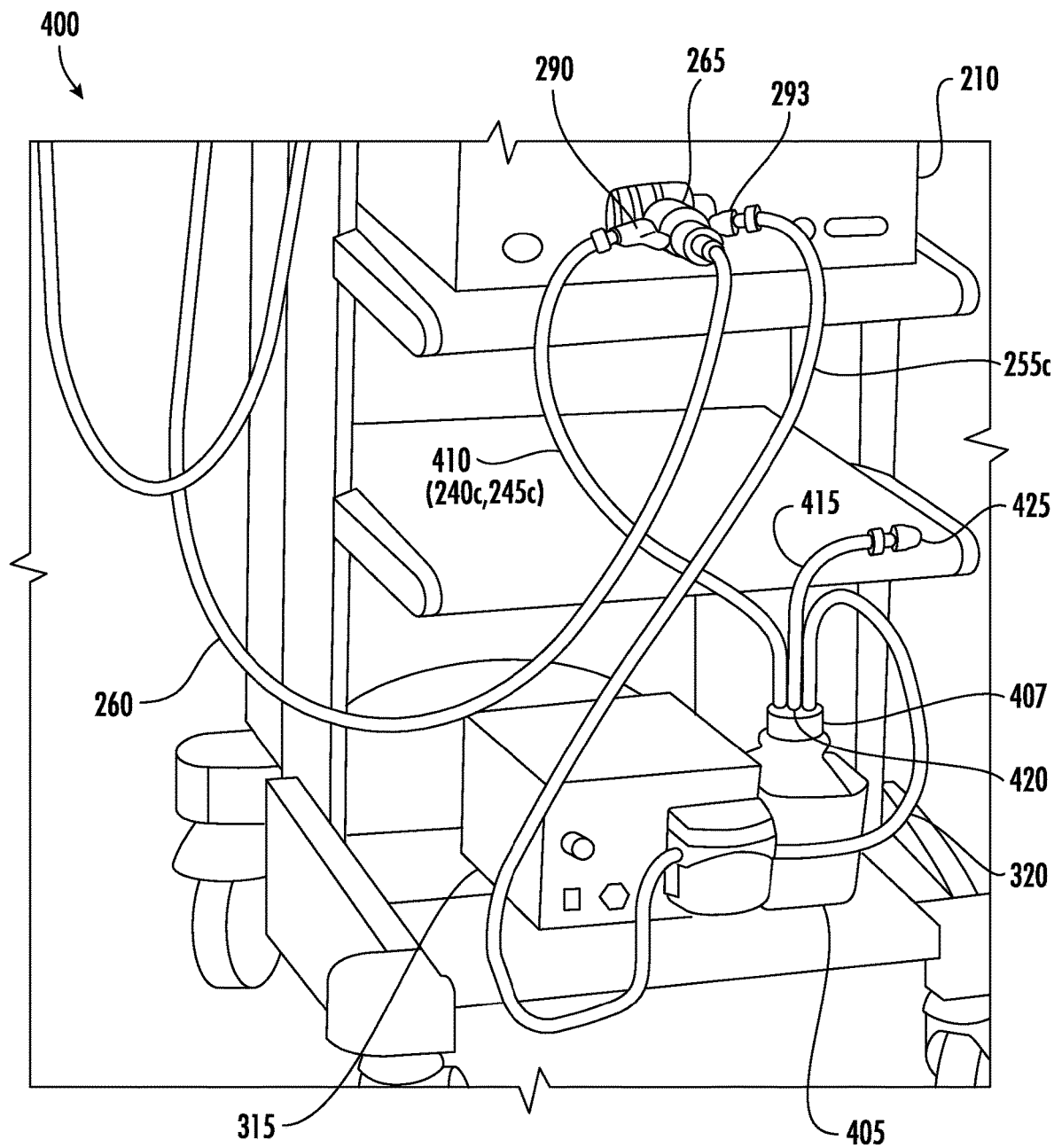
FIG. 4 illustrates an endoscope system with endoscope, light source, water reservoir, and tubing assembly for hybrid air/lens wash, irrigation, and gas fluid delivery.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255c, and alternative gas supply tubing 415 (e.g., $CO_2$). A portion of the alternative gas supply tubing 415 passes from one end positioned in the gas gap 275 between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. In the neutral state, $CO_2$ gas flows backward up the gas supply tubing 240c to the connector portion 265, up the gas feed line 240b, and is vented through the gas/water valve 140 to atmosphere. In the first position, the user closes off the vent hole in the gas/water valve 140, and the $CO_2$ gas is flowed through the gas/water valve to the gas supply line 240a in the endoscope shaft 100a and out the gas/lens wash nozzle 220 at the distal tip 100c. In the second position, the user depresses the valve 140 to the bottom of the valve well 135, keeping the vent hole in the gas/water valve closed off. The second position blocks the $CO_2$ gas supply to both atmosphere and the gas supply line 240a in the endoscope 100, and opens up the gas/water valve 140 to allow lens wash water to pass through to the lens wash supply line 245a in the endoscope shaft 100a and out the gas/lens wash nozzle 220 at the distal tip 100c. Gas (pressure) in the reservoir 405 is maintained by delivery of gas through alternative gas (e.g., $CO_2$) supply tubing 415. The irrigation function may be accomplished in a similar manner as the operation described above with respect to FIG. 3D.

Several challenges may exist with respect the systems discussed above in reference to FIGS. 1-4. For example, with non-hybrid systems that do not consolidate fluid requirements in a single fluid source, if a user wants to provide lens wash and irrigation during an endoscopic procedure, one bottle may be required to provide lens wash fluid, while a separate bottle is used for irrigation fluid. This may not be the most efficient in terms of having to fill/refill multiple bottles, the cost and space requirements of using multiple bottles instead of a single fluid reservoir, etc. Conversely, when considering a hybrid system with a single fluid reservoir, consolidating the lens wash and irrigation function in a single bottle may result in as many as four openings in the bottle cap, and up to four sets of tubing being passed through the openings. For example, irrigation and lens wash may have separate tubing, and gas supply used to pressurize the reservoir, in order to deliver the flow of lens wash may have separate tubing. Typically, the gas supply is air delivered from an air pump that is included in the video processing unit for the endoscope system. If an alternate gas supply, such as $CO_2$, is desired, that gas source is typically found in endoscopy suites ("house gas") and require another set of tubing. In some cases, the lens wash and gas supply from the endoscope may be arranged coaxially to each other, which reduces the required cap openings to three, but still requires separate tubing (e.g., FIG. 4). Each of the openings is required to be sealed in order for the reservoir to maintain pressure, and tubing systems with such arrangements are typically provided with the various tubing already threaded through the cap. Accordingly, for a user that may want to use a tubing set for only lens wash, the set may also include openings and tubing for irrigation and an alternate gas supply extending unused out of the bottle. This tubing has to be clamped off or otherwise closed to maintain pressure. The unused tubing may also present handling changes, resource cost, etc. As such, the advantages of a single fluid reservoir that also addresses the challenges of a cap with multiple openings and multiple portions of tubing passing through the cap, could be beneficial in terms of efficient cost, set-up, handling, flexibility, etc.

Addressing these considerations, and in accordance with general principles of the present disclosure, improved tubing assemblies are described, including endoscope systems incorporating the tubing assemblies and methods for distributing fluid between an endoscope and a fluid reservoir in the endoscope systems, utilizing embodiments of the tubing assemblies. In general terms, tubing assemblies according to embodiments of the present disclosure may comprise a tubing manifold in fluid communication with a source or reservoir of fluid, such as a water reservoir, bottle, container, etc. (such terms being used interchangeably without intent to limit or otherwise convey different meaning or intent) and a source or sources of one or more gases via portions of tubing, tubing sets or tube sets (such terms being used interchangeably without intent to limit or otherwise convey different meaning or intent). The manifold may be arranged and configured to reside in fluid communication between the endoscope and the fluid reservoir and apart from the fluid reservoir allowing, among other advantages, for different portions of tubing for the various functions discussed above (e.g., lens wash, irrigation, gas supply, and alternate gas supply) to be managed efficiently with reduced openings and/or tubing portions having to be accommodated through a cap on the reservoir.

In embodiments, tubing assemblies in various configurations, in addition to the manifold, may include a portion of gas supply tubing configured for connection in fluid communication between the manifold and an endoscope, a portion of lens wash supply tubing configured for connection in fluid communication between the manifold and the endoscope, a cap configured to be removably attached to a fluid reservoir, a portion of gas supply tubing configured for connection in fluid communication between the cap and the manifold, and a portion of lens wash (e.g., liquid) supply tubing configured for connection in fluid communication between the fluid reservoir and the manifold. Portions of irrigation (e.g., liquid) tubing and alternate gas supply tubing may be included as well, in some cases, as optionally and/or removably connectable to the manifold rather than being required in the assemblies, such as a customizable or modular tubing assembly or system. Such customizable or modular assemblies or systems may have one or more advantages of allowing users to selectively choose which type and/or number of tubing and/or fittings/filters/valving to use in a given procedure depending on various procedure requirements or desires. This flexibility and control may allow efficiencies, such as reducing price, saving material, and manufacturing costs, improving procedure set-up and total time, disposability (e.g., singe use), minimizing waste of unused tubes, expanding compatibility across various endoscope systems, etc., compared to present systems that are typically configured with each type of tubing regardless if all paths are needed or desired. As such, embodiments with kits that may include the manifold, portions of tubing which may be optionally connected, as desired by the user, to manage irrigation and an alternate gas supply, fittings (e.g., valves, filters, adaptors) for use with the tubing portions, and endoscope procedures and systems, implementing such tubing assemblies, are contemplated within the scope of the present disclosure.

Further, in many embodiments formed in accordance with principles of the present disclosure, aspects of the present disclosure may include tubing systems and/or assemblies that result in more efficient and/or environmentally friendly endoscope systems. In several embodiments, the tubing systems and/or assemblies may reduce waste, such as by facilitating reusability. In some embodiments, the tubing systems and/or assemblies may decrease associated logistical and storage costs. For example, the reservoir may be collapsible to reduce volume needed to store or package the tubing systems and/or assemblies. In various embodiments, the tubing systems and/or assemblies may reduce manufacturing complexity. For example, integrally forming one or more components can reduce assembly steps. In various embodiments, components of the tubing systems and/or assemblies may include features to reduce cleaning and/or processing time, such as between procedures. For example, coaxial tubing may reduce the amount of surface area that must be cleaned.

Figure 5A:
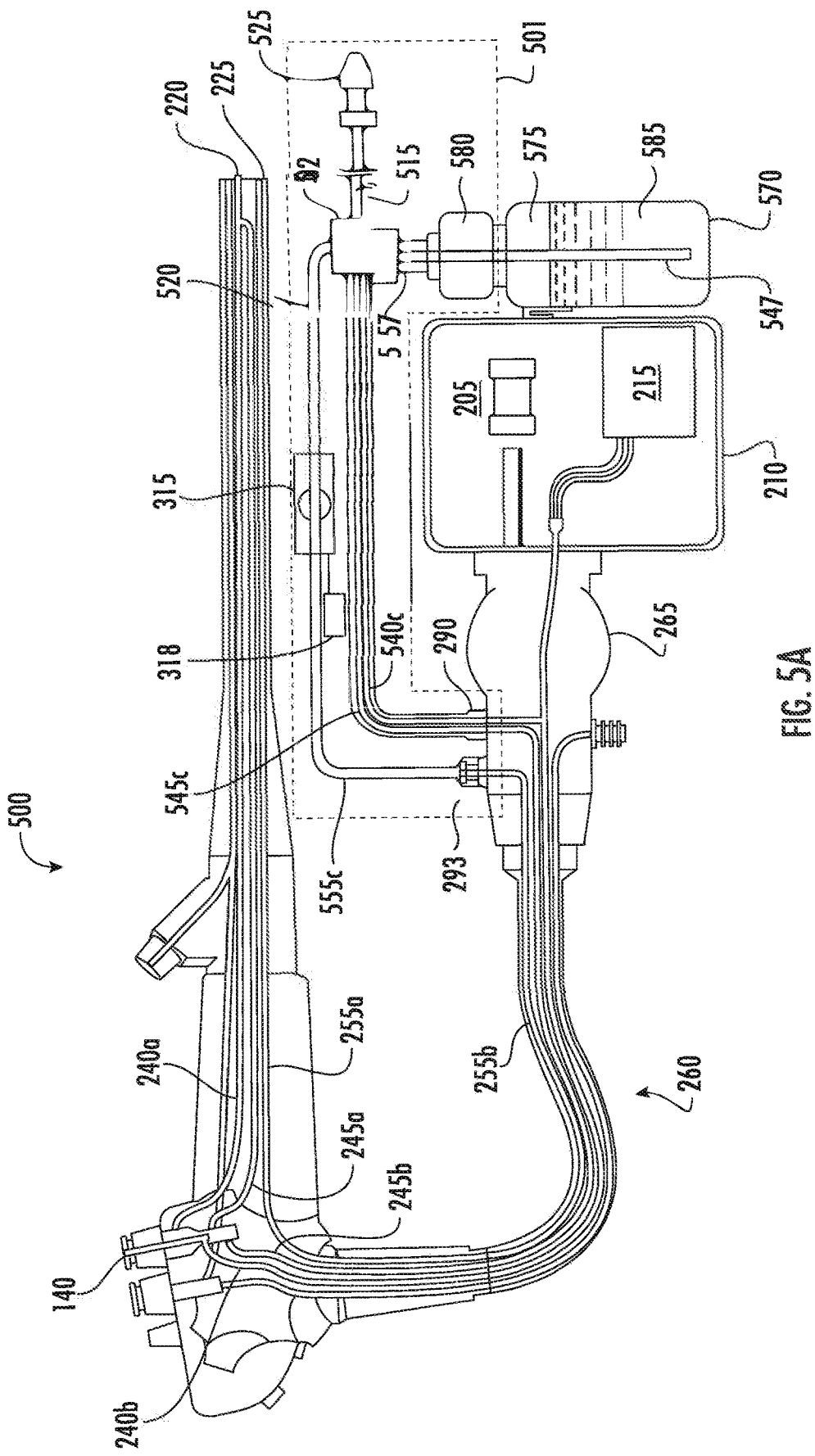
FIG. 5A illustrates an endoscope system with endoscope, light source, fluid reservoir, and tubing assembly, according to an embodiment of the present disclosure.

Referring to FIG. 5A, a tubing system 500 in accordance with embodiments of the present disclosure is illustrated. The system comprises a tubing assembly 501, arranged and configured for distributing fluid during an endoscopic procedure. The system apart from the tubing assembly includes components similar to the endoscope and endoscope systems described with regard to FIGS. 1-4; however, not all features may be described or shown here if not pertinent to the fluid circuit of the system. The endoscope is shown with the shaft, handle portion, umbilicus 260, connector portion 265, video processing unit 210, and fluid reservoir 570. The fluid reservoir is depicted as partially filled with fluid resulting in remaining fluid 585 at the bottom of the reservoir 570 and a gap 575 at the top of the reservoir, which may be filled with a gas to pressurize the reservoir when it is sealed. The video processing unit 210 may include light source 205 and gas (e.g., air) pump 215. Portions of tubing may be provided from the video processing unit 201 and the connector portion 265 through the umbilicus 260 to the endoscope handle portion, in order to delivery fluids to the endoscope for use during a patient procedure.

Fluid as a gas supply for insufflating a patient (e.g., air from pump 215, $CO_2$ from an alternate gas source (not shown) may be provided through gas supply line 240a and gas feed line 240b, which are in fluid communication and extend, respectively, downstream, and upstream of gas/water valve 140. Gas travels through gas feed line 240b along umbilicus 260, through valve 140 and exits gas supply line 240a, extending along the shaft of the endoscope, through gas/lens wash nozzle 220. Fluid, e.g., water, as a lens wash supply from reservoir 570 for clearing an imaging lens at the distal end of the patient may be provided through lens wash supply line 245a and lens wash feed line 245b, which are in fluid communication and extend, respectively, downstream, and upstream of gas/water valve 140. Lens wash travels through lens wash feed line 245b along umbilicus 260, through valve 140 and exits lens wash supply line 245a, extending along the shaft of the endoscope, through gas/lens wash nozzle 220. Gas/water valve 140 may be actuated by user to switch between delivery of gas supply and delivery of lens wash supply by, e.g., respectively covering and depressing valve 140 downward. Fluid, e.g., a liquid or water, as an irrigation supply from reservoir 570 may be provided as a higher volume and/or flow rate of fluid, compared to the lens wash supply, for purposes of irrigating or removing debris in front of the endoscope. Irrigation fluid may be provided through irrigation supply line 255a and irrigation feed line 255b, which are in fluid communication and extend along umbilicus 260. Irrigation fluid supply exits the endoscope along irrigation supply line 255a, extending along the shaft of the endoscope, and through irrigation opening 225. Irrigation (e.g., peristaltic) pump 315, actuated with foot switch 318, may be placed in line to pump irrigation fluid from the reservoir 570 and delivery it through the endoscope to the patient.

Tubing assembly 501, as part of endoscope system 500, may include the components represented within the dotted line border of FIG. 5A. Fluid reservoir 570 is shown with reservoir top 580, which may be removably attachable to the remaining bottom portion of reservoir 570 (e.g., in a bottle and threaded cap arrangement). Top 580 maybe removably attached in order to replenish fluid in the reservoir when it becomes depleted. Alternatively, reservoir bottom and top 580 may be sealed to each other or they may be manufactured as a single, integral body (e.g., similar to a sealed monolithic rigid or semi-rigid bottle or softer IV bag or pouch). In such embodiments, a fill port may be included on another part of the reservoir for replenishing fluid.

Reservoir top 580 may be connected in fluid communication with tubing manifold 502 via a portion of shared gas supply/alternate gas supply tubing 557. The same portion of shared tubing 557 extends from an opening of manifold 502 through a single reservoir opening 548 (see FIG. 5B) in reservoir top 580, terminating in reservoir gap 575, at or below the top opening 548, but not extending into the remaining fluid 585 in the reservoir 570. Reservoir top 580 may also be connected in fluid communication with tubing manifold 502 via a portion of shared lens wash supply/irrigation supply tubing 547. The same portion of shared tubing 547 extends from an opening of manifold 502 through the single reservoir opening 548 in top 580, terminating in the remaining fluid 585 at or substantially at the bottom of reservoir 570. In the arrangement shown in FIG. 5A, the portion of shared lens wash supply and irrigation supply tubing 547 is arranged coaxially within the shared gas supply/alternate gas supply tubing 557, leaving an annular gap between the tubing portions, such that a gas supply from air pump 215 or an alternate gas source may flow through the portion of tubing 557, around the portion of tubing 547 into gap 575, pressurizing the remaining fluid 585 in reservoir 570, and forcing the fluid up through the portion of shared lens wash/irrigation supply tubing 547 to manifold 502. Although shown in a coaxial arrangement, it may be possible for the shared portion of gas/alternate gas supply tubing 557 to extend through an opening in top 580 to an opening in manifold 502, while shared portion of lens wash/irrigation supply tubing 547 extends through a separate opening in top 580 to a separate opening in manifold 502.

Tubing assembly 501 may also include a portion of alternate gas supply tubing 515 extending from an alternate gas source (not shown) to an opening of tubing manifold 502. Alternate gas supply tubing 515 may include a fitting 525 at a gas source end of the portion of tubing 515. The fitting may be one or more of a valve, an adaptor, a filter, etc., for one or more of a variety of uses, such as filtering particulate in the fluid, closing off flow through the tubing, preventing flow through the tubing in a certain direction, adapting to a source fitting, etc., and the like, as further described below with respect to FIGS. 7-9.

A portion of gas supply tubing 540c and a portion of lens wash supply tubing 545c may extend from an opening of manifold 502, respectively, and may be connected in fluid communication with the endoscope at gas/lens wash connection 290 on connector portion 265 of umbilicus 260. The portion of gas supply tubing 540c is connected in fluid communication with gas pump 215 and gas feed line 240b, and the portion of lens wash supply tubing 545c is connected in fluid communication with lens wash fee line 245b, within connector portion 265. The portion of gas supply tubing 540c is in fluid communication through tubing manifold 502 with the portion of shared gas supply/alternate gas supply tubing 557. Similarly, the portion of lens wash supply tubing 545c is in fluid communication through tubing manifold 502 with the portion of shared lens wash/irrigation supply tubing 547.

A portion of upstream irrigation supply tubing 520 extending from an opening of manifold 502 is in fluid communication with a portion of downstream irrigation supply tubing 555c. The portion of irrigation supply tubing 520 is upstream of an inlet to pump 315 and is in fluid communication through manifold 502 with the portion of shared lens wash supply and irrigation supply tubing 547. The portion of irrigation supply tubing 555c is downstream of an outlet to pump 315 and is connected in fluid communication with the endoscope at irrigation connection 293 on connector portion 265 of umbilicus 260. The portion of irrigation supply tubing 555c is connected in fluid communication with irrigation feed line 255b, within connector portion 265.

Figure 5B:
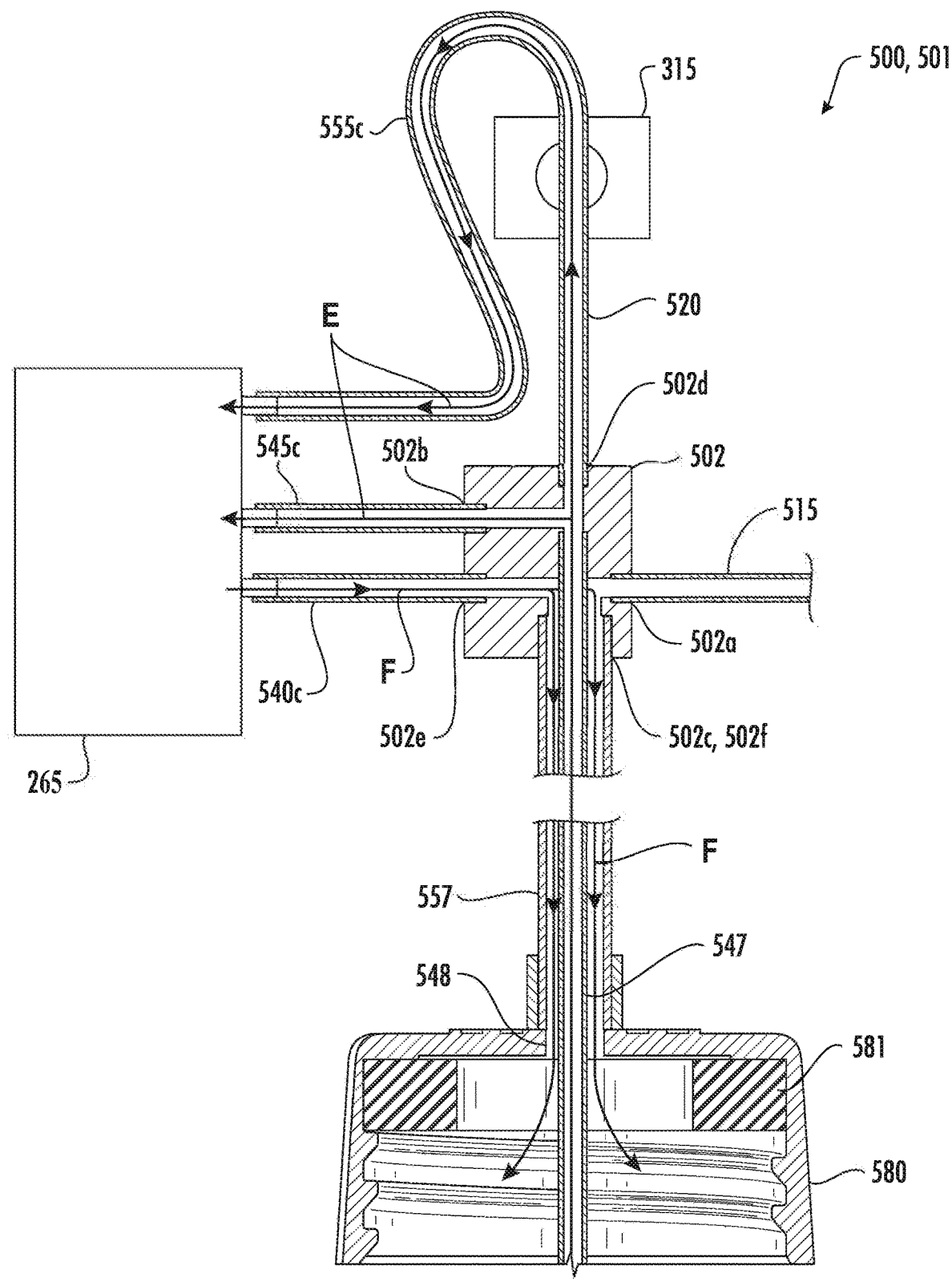
FIG. 5B illustrates a cross-sectional view of a tubing assembly suitable for use with the endoscope system of FIG. 5A, with a tubing manifold, a reservoir cap, and tubing, wherein the flow path of gas supply is activated to deliver lens wash and/or irrigation fluid through the patient end of the endoscope, according to an embodiment of the present disclosure.
Figure 5C:
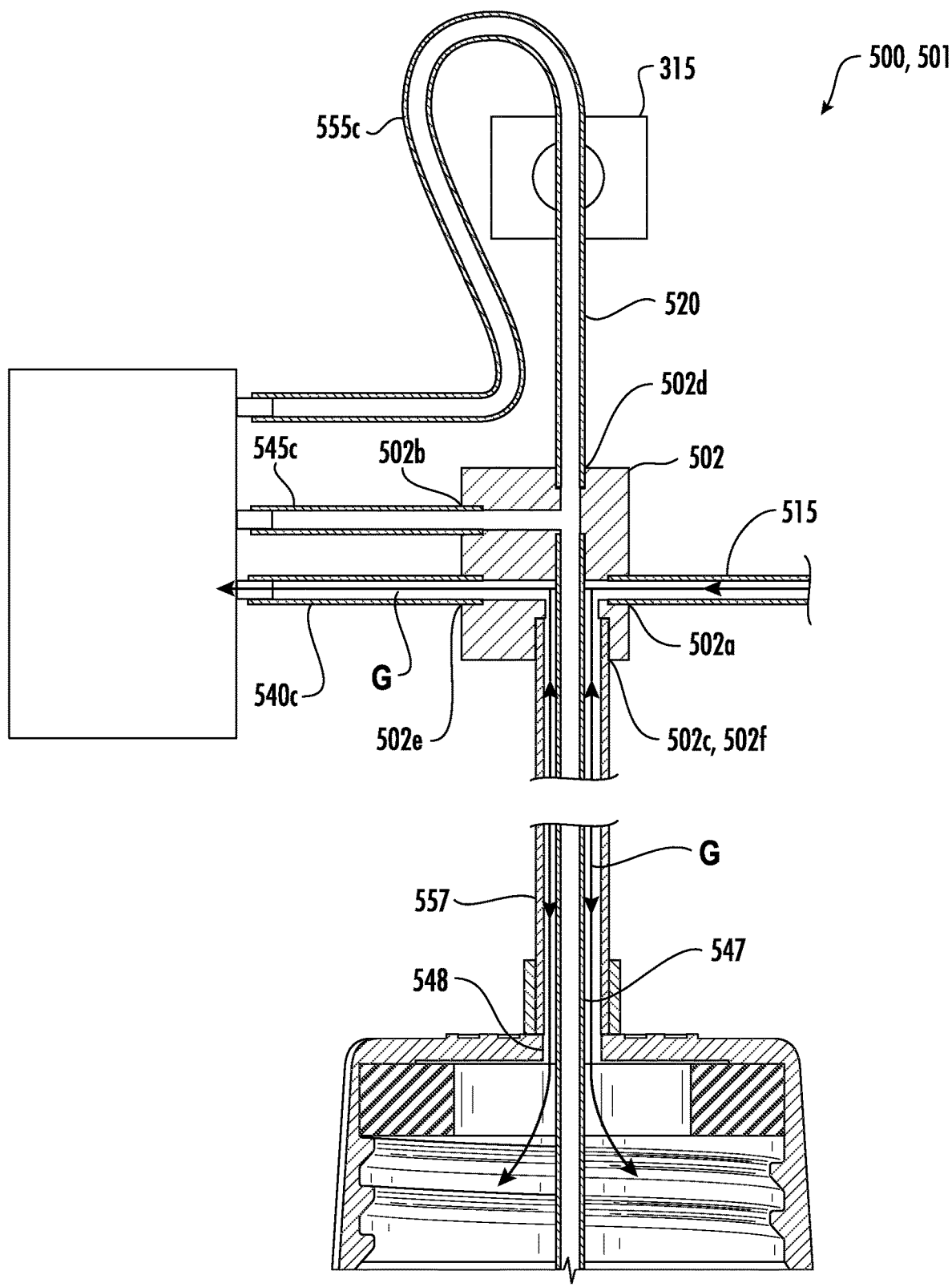
FIG. 5C illustrates a cross-sectional view of the tubing assembly of FIG. 5B, wherein the flow of an alternate gas supply is activated to deliver lens wash and/or irrigation fluid through the patient end of the endoscope, according to an embodiment of the present disclosure.

Referring to FIGS. 5B-5C, a cross-sectional view of an embodiment of the tubing assembly 501 of system 500 of FIG. 5A is described in further detail. Tubing manifold 502, reservoir cap 580 and various portions of supply tubing may be connected in fluid communication between an alternate gas source (not shown) and manifold 502, between manifold 502 and fluid reservoir 570, and between manifold 502 and video processing unit 210 of the endoscope. Manifold 502 may have a number of openings 502a, 502b, 502c, 502d, 502e, 502f, arranged and configured to receive manifold ends of the portions of gas supply tubing 540c, upstream irrigation supply tubing 520, lens wash supply tubing 545c, and alternate gas supply tubing 515, as well as the manifold ends of the portion of shared lens wash/irrigation supply tubing 547 and the portion of shared lens wash/irrigation supply tubing 547.

In embodiments, reservoir top 580 may be a threaded cap removably attached to the remaining portion of reservoir 570. The cap may be arranged and configured to be compatible with a single type of reservoir (e.g., bottle type), or compatible with different types of reservoirs (e.g., universal threading to accept different bottle types). In removable embodiments, top 580 may include reservoir gasket 581 to help ensure a pressure-tight seal within the reservoir, when attached.

The portion of shared lens wash/irrigation supply tubing 547 extends through reservoir opening 548 to the manifold end of the tubing connected in fluid communication within lens wash/irrigation opening 502c in manifold 502. The portion of shared gas/alternate gas supply tubing 557 extends through reservoir opening 548 to the manifold end of the tubing connected in fluid communication within gas/alternate gas opening 502f in manifold 502. In the coaxial arrangement of the portion of shared lens wash/irrigation supply tubing 547 within the portion of shared gas/alternate gas supply 557, as shown, opening 502c may similarly be coaxial with opening 502f. Further, as shown, the portion of gas supply tubing 540c extends from the endoscope to the manifold end of the tubing connected in fluid communication within gas/alternate gas opening 502e in manifold 502, the portion of lens wash supply tubing 545c extends from the endoscope to the manifold end of the tubing connected in fluid communication within lens wash opening 502b in manifold 502, the downstream portion of irrigation tubing 555c extends from the endoscope to the outlet of the irrigation pump 315 and the upstream portion of irrigation tubing 520 extends from the inlet of the pump to the manifold end of the tubing 520 connected in fluid communication within irrigation opening 502d in manifold 502, and the portion of alternate gas supply tubing 515 extends from the alternate gas source (not shown) to the manifold end of the tubing connected in fluid communication within alternate gas opening 502a in manifold 502.

Certain of the openings 502a-502f in the manifold 502 may be fluidly connected through channels in the manifold with other of the openings 502a-502f in the manifold to establish flow paths for the gas supply, alternate gas supply, irrigation supply and/or lens wash supply. For example, as shown in FIG. 5B, with respect to flow path F for gas supply, openings 502a, 502e, and 502f are fluidly connected to each other through a common channel within manifold 502. Further, as shown in FIG. 5B, with respect to flow path E for lens wash and irrigation supply, openings 502b, 502c, and 502d are fluidly connected to each other through a common channel in manifold 502.

In embodiments, the use of tubing assembly 501, with an endoscope during a procedure with a fluid circuit having the same or similar tubing as system 500, may follow flow paths E and F depicted in FIG. 5B. For example, with respect to flow path F, when air pump 215 is activated and gas/lens wash valve 140 is depressed, air flows from video processing unit 210, along the portion of gas supply tubing 540c through opening 502e of the manifold, exits the manifold through opening 502f and flows along the portion of shared gas/alternate gas supply tubing 557 through opening 548 in cap 580 and into the gap 575 in fluid reservoir 570. Flow from alternate gas source through tubing 515 and opening 502a is closed off, allowing the gas supply to pressurize the fluid reservoir. Further, with respect to flow path E, when the gas supply pressurizes the fluid reservoir, fluid is forced along the portion of shared lens wash/irrigation supply tubing, through opening 548 in cap 580, and enters the manifold through opening 502c. In the absence of irrigation pump 315 being activated or irrigation supply tubing not being used or closed off (e.g., a seal or membrane, fitting or valve, as described below), fluid continues to flow as lens wash fluid, exiting opening 502b and flowing along tubing 545c to the connector portion 265 of umbilicus 260 connected to video processing unit 210. In the event a portion of irrigation supply tubing 520 is connected to manifold 502 and is open to flow when irrigation pump 315 is activated, fluid is drawn from fluid reservoir along the path as lens wash fluid into the manifold, at which point it branches off from the lens wash fluid path and exits through opening 502d, along the upstream portion of irrigation supply tubing 520, and is pumped through the downstream portion of irrigation supply tubing 555c to the connector portion 265 of umbilicus 260 connected to video processing unit 210. Fluid for irrigation may be drawn by the pump from the fluid reservoir at the same time as fluid for lens wash is pushed to the endoscope by the gas supply, or the functions may be performed separately.

Referring to FIG. 5C, in embodiments, the use of tubing assembly 501, with an endoscope during a procedure with a fluid circuit the same or similar to tubing system 500, may follow flow path G depicted in FIG. 5C. The configuration of the tubing assembly 501 and system 500 in FIG. 5C, is the same as the configuration of FIG. 5B, so for the sake of brevity, a detailed description of similar elements is omitted herefrom. With respect to flow path F, depicted in FIG. 5C, when air pump 215 is de-activated and gas/lens wash valve 140 is depressed, an alternate gas supply (e.g., $CO_2$) is open to flow from alternate gas source (not shown), along the portion of alternate gas supply tubing 515 through opening 502a of the manifold, exits the manifold through opening 502f and flows along the portion of shared gas/alternate gas supply tubing 557 through opening 548 in cap 580 and into the gap 575 in fluid reservoir 570. Since flow from the gas supply in the endoscope (air pump 215) is closed off, flow from the alternate gas supply into the fluid reservoir 570 pressurizes the fluid remaining 585 in the reservoir, in the same manner as the gas supply from the endoscope along flow path F in FIG. 5B. The flow of fluid as lens wash and/or irrigation operates in the same manner as well along the same path E shown in FIG. 5B. The flow of the alternate gas supply is also available to flow in an opposite or reverse direction along flow path F to the connector portion 265 connected to video processing unit 210 of the endoscope, when a user activates gas/lens wash valve 140 to provide the alternate gas supply through the endoscope to the patient for use, e.g., as an insufflating gas, rather than calling for lens wash fluid.

Figure 6A:
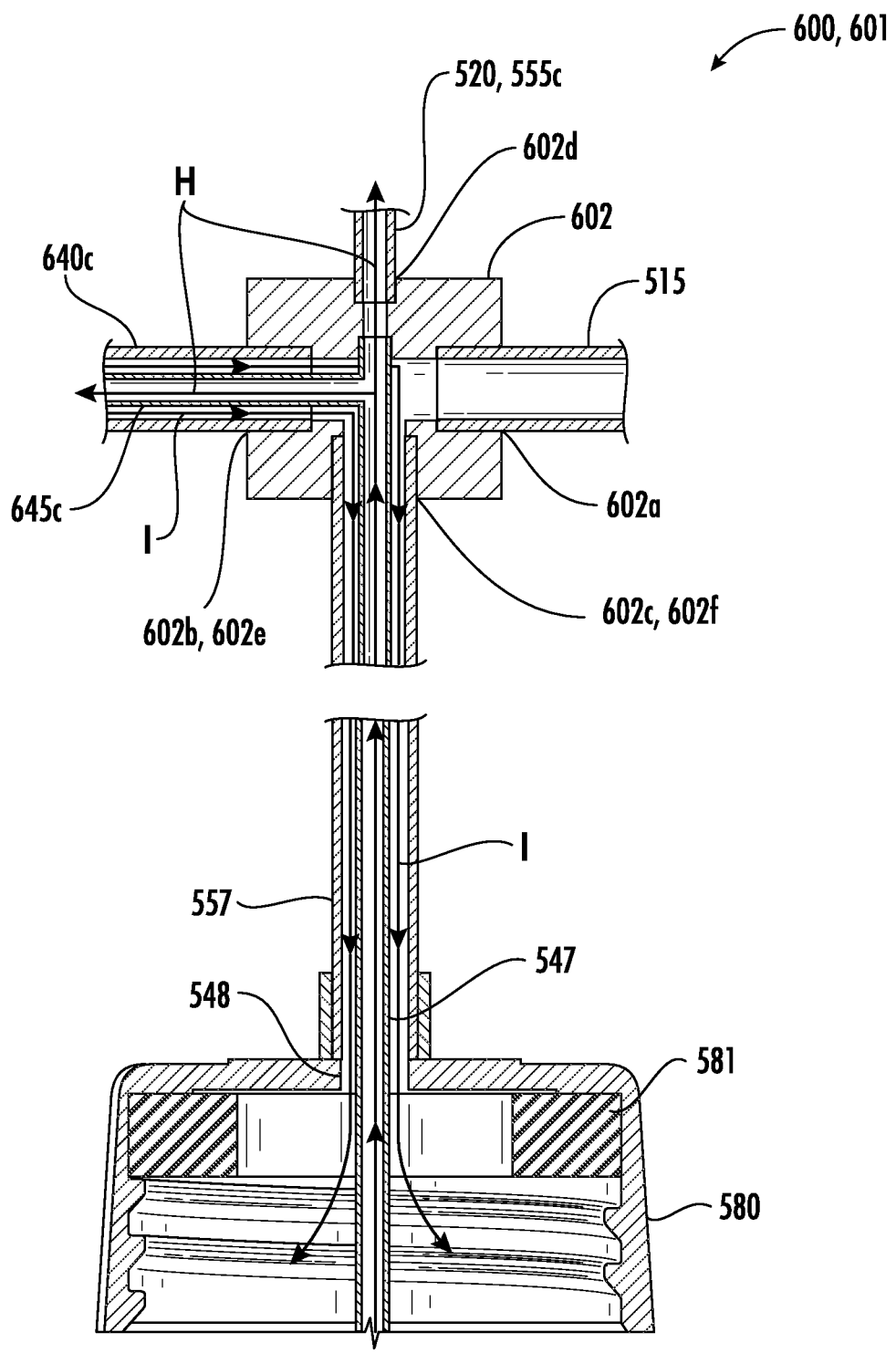
FIG. 6A illustrates a cross-sectional view of a tubing assembly suitable for use with the endoscope system of FIG. 5A, with a manifold, a reservoir cap, and tubing, wherein the flow path of gas supply is activated to deliver lens wash and/or irrigation fluid through the patient end of the endoscope, according to an embodiment of the present disclosure.
Figure 6B:
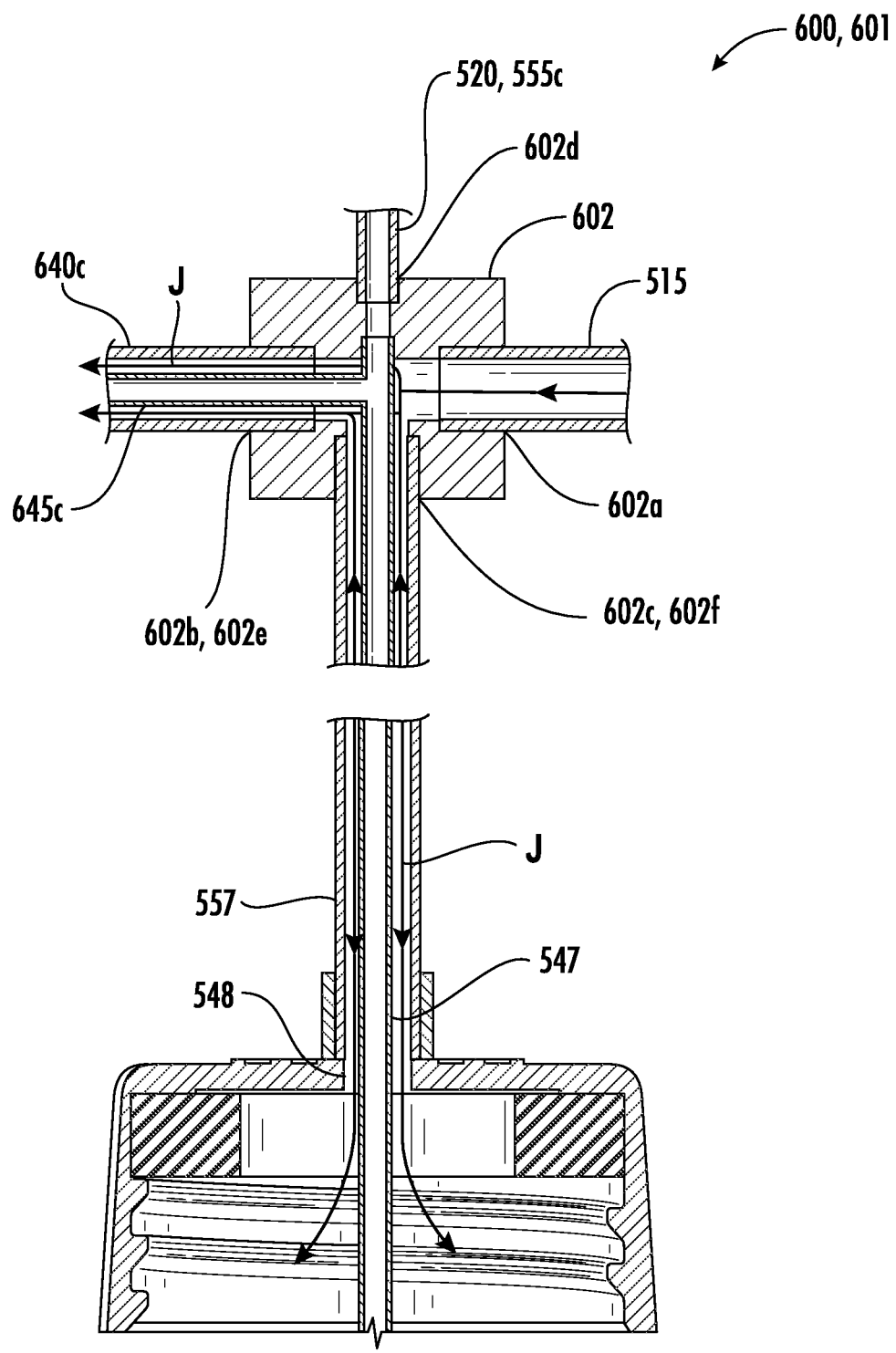
FIG. 6B illustrates a cross-sectional view of the tubing assembly of FIG. 6A, wherein the flow path of gas supply is activated to deliver lens wash and/or irrigation fluid through the patient end of the endoscope, according to an embodiment of the present disclosure.

Referring to FIGS. 6A-6B, a cross-sectional view of an alternative embodiment of a tubing assembly 601 is described in further detail. The tubing assembly 601 may be suitable for use in a system 600, which may be configured and arranged in a manner that is the same as or substantially similar to system 500 in FIG. 5A. As such, for sake of brevity, a detailed description of some similar elements may be omitted herefrom. Tubing manifold 602, reservoir cap 580 and various portions of supply tubing may be connected in fluid communication between an alternate gas source (not shown) and manifold 602, between manifold 602 and fluid reservoir 570, and between manifold 602 and connector portion 265 of umbilicus 260 connected to video processing unit 210 of the endoscope (not shown). Manifold 602 may have a number of openings 602a, 602b, 602c, 602d, 602e, 602f, arranged and configured to receive manifold ends of the portions of gas supply tubing 640c, upstream irrigation supply tubing 520, lens wash supply tubing 645c, and alternate gas supply tubing 515, as well as the manifold ends of the portion of shared lens wash/irrigation supply tubing 547 and the portion of shared lens wash/irrigation supply tubing 547.

The portion of shared lens wash/irrigation supply tubing 547 extends through reservoir opening 548 to the manifold end of the tubing connected in fluid communication within lens wash/irrigation opening 602c in manifold 602. The portion of shared gas/alternate gas supply tubing 557 extends through reservoir opening 548 to the manifold end of the tubing connected in fluid communication within gas/alternate gas opening 602f in manifold 602. In the coaxial arrangement of the portion of shared lens wash/irrigation supply tubing 547 within the portion of shared gas/alternate gas supply 557, as shown, opening 602c may be similarly coaxial with opening 602f. Further, as shown, the portion of gas supply tubing 640c extends from the endoscope to the manifold end of the tubing connected in fluid communication within gas supply opening 602e in manifold 602, the portion of lens wash supply tubing 645c extends from the endoscope to the manifold end of the tubing connected in fluid communication within lens wash opening 602b in manifold 602. In the arrangement shown in FIG. 6A, the portion of lens wash supply tubing 645c is arranged coaxially within the portion of gas supply tubing 640c, leaving an annular gap between the tubing portions, such that a gas supply from air pump 215 or an alternate gas supply from the portion of alternate gas supply tubing 515 may flow through the portion of gas supply tubing 640c, around the portion of lens wash supply tubing 645c. In this coaxial arrangement of the portion of lens wash supply tubing 645c within the portion of gas supply tubing 640c, as shown, opening 602b may similarly be coaxial with opening 602e.

The downstream portion of irrigation tubing 555c extends from the endoscope to the outlet of the irrigation pump 315 (not shown) and the upstream portion of irrigation tubing 520 extends from the inlet of the pump to the manifold end of the tubing 520 connected in fluid communication within irrigation opening 602d in manifold 602, and the portion of alternate gas supply tubing 515 extends from the alternate gas source (not shown) to the manifold end of the tubing connected in fluid communication within alternate gas opening 602a in manifold 602.

Certain of the openings 602a-602f in the manifold 602 may be fluidly connected through channels in the manifold with other of the openings 602a-602f in the manifold to establish flow paths for the gas supply, alternate gas supply, irrigation supply and/or lens wash supply. For example, as shown in FIG. 6A, with respect to flow path I for gas supply, openings 602a, 602e, and 602f are fluidly connected to each other through a common channel within manifold 602. Further, as shown in FIG. 6A, with respect to flow path H for lens wash and irrigation supply, openings 602b, 602c, and 602d are fluidly connected to each other through a common channel in manifold 602.

In embodiments, the use of tubing assembly 601, with an endoscope during a procedure with a fluid circuit the same or similar to tubing system 500, 600, may follow flow paths H and I depicted in FIG. 6A. For example, with respect to flow path I, when air pump 215 is activated and gas/lens wash valve 140 is depressed, air flows from video processing unit 210 (not shown), along the portion of gas supply tubing 640c through opening 602e of the manifold, exits the manifold through opening 602f and flows along the portion of shared gas/alternate gas supply tubing 557 through opening 548 in cap 580 and into the gap 575 in fluid reservoir 570. Flow from alternate gas source through tubing 515 and opening 602a is closed off, allowing the gas supply to pressurize the fluid reservoir. Further, with respect to flow path H, when the gas supply pressurizes the fluid reservoir, fluid is forced along the portion of shared lens wash/irrigation supply tubing, through opening 548 in cap 580, and enters the manifold through opening 602c. In the absence of irrigation pump 315 being activated or irrigation supply tubing not being used or closed off (e.g., by a seal or membrane, fitting or valve, as described below), fluid continues to flow as lens wash fluid, exiting opening 602b and flowing along tubing 645c to the connector portion 265 of umbilicus 260 connected to video processing unit 210. In the event a portion of irrigation supply tubing 520 is connected to manifold 602 and is open to flow when irrigation pump 315 is activated, fluid is drawn from fluid reservoir along the path as lens wash fluid into the manifold, at which point it branches off from the lens wash fluid path and exits through opening 602d, along the upstream portion of irrigation supply tubing 520, and is pumped through the downstream portion of irrigation supply tubing 555c to the connector portion 265 of umbilicus 260 connected to video processing unit 210 (not shown). Fluid for irrigation may be drawn by the pump from the fluid reservoir at the same time as fluid for lens wash is pushed to the endoscope by the gas supply, or the functions may be performed separately.

Referring to FIG. 6B, in embodiments, the use of tubing assembly 601, with an endoscope during a procedure with a fluid circuit the same or similar to tubing system 500, 600, may follow flow path J depicted in FIG. 6B. The configuration of the tubing assembly 601 and system 600 in FIG. 6B, is the same as the configuration of FIG. 6A, so for the sake of brevity, detailed description of similar elements is omitted herefrom. With respect to flow path J, depicted in FIG. 6B, when air pump 215 is de-activated and gas/lens wash valve 140 is depressed, an alternate gas supply (e.g., $CO_2$) is open to flow from alternate gas source (not shown), along the portion of alternate gas supply tubing 515 through opening 602a of the manifold, exits the manifold through opening 602f and flows along the portion of shared gas/alternate gas supply tubing 557 through opening 548 in cap 580 and into the gap 575 in fluid reservoir 570. Since flow from the gas supply in the endoscope (air pump 215) is closed off, flow from the alternate gas supply into the fluid reservoir 570 pressurizes the fluid remaining 585 in the reservoir, in the same manner as the gas supply from the endoscope along flow path I in FIG. 6A. The flow of fluid as lens wash and/or irrigation operates in the same manner as well along the H path shown in FIG. 6A. The flow of the alternate gas supply is also available to flow in an opposite or reverse direction along flow path J to the connector portion 265 connected to video processing unit 210 of the endoscope, when a user activates gas/lens wash valve 140 to provide the alternate gas supply through the endoscope to the patient for use, e.g., as an insufflating gas, rather than calling for lens wash fluid.

Other arrangements and configurations of openings, portions of supply tubing, fluid reservoir, reservoir caps, or manifold, or combinations thereof, and the like forming a tubing assembly for use within tubing systems, as desired for particular applications, are contemplated within the present disclosure. For example, one or more of the features and components described with respect to FIGS. 6B-8 may be utilized in conjunction with, or incorporated into, one or more of the embodiments of FIGS. 10-12. The manifold 502, 602 shown as a square block in FIGS. 5A-6B, may be configured in any shapes, and with any dimensions, that are suited to desired applications. The manifold may be injection molded or formed by other known manufacturing techniques. The material of the manifold may be various types of polymer, or metal, suitable for single, disposable use. The various portions of tubing described may be secured within the openings by adhesive, ultrasonic welding, or other known manufacturing techniques. In some embodiments, such as customizable or modular tubing assemblies, or tubing manifolds, the irrigation supply and/or alternate gas supply tubing may be provided in a tubing kit as tubing that is selectively connectable to the manifold. In such embodiments, the openings of the manifold that receive the irrigation and alternate supply tubing may be provided with a seal or membrane that is puncturable in use by a penetrating element of the tubing. In other embodiments, a fitting that is switchable between a closed and open position may be used as an alternative or in addition to a puncturable seal or membrane to close-off flow through the openings when the optional tubing is not being used.

In embodiments, each of the various portions of supply tubing may include a manifold or cap end including a piercing or penetrating member arranged and configured to pierce a membrane or seal of corresponding openings 502a-502f, 602a-602f of manifold 502, 602, or additionally or alternatively, opening 548 of cap 580, as the tubing or coaxial tubing is being inserted, pressed, etc. into the seal or membrane to open the opening for flow through the connected tubing. The portions of tubing may be sealed to maintain a sterile environment prior to use. In addition, and/or alternatively, each of the portions of tubing may include, for example, a one-way valve (e.g., FIG. 9), to prevent backflow into the fluid reservoir during use. For example, in one embodiment, each of the portions of tubing may include a one-way valve in an end of the portions of tubing opposing the manifold end to prevent backflow of fluid into the container during use. In addition, and/or alternatively, one or more of the portions of tubing may include a connector or adapter such as, for example, a Tuohy Borst connector, an adjustable connector such as, for example, stop-cock adaptor, a split connector such as, for example, a coaxial split connector or scope adapter arranged and configured to couple to the connector portion 265 of the endoscope, etc., of system 500, 600. In use, the adapters may be arranged and configured in a normally closed position to maintain the sterile environment prior to use. Thereafter, during use, as needed, the user can move one or more of the adapters from the closed position to an opened position to enable flow of fluid as needed.

Figure 7A:
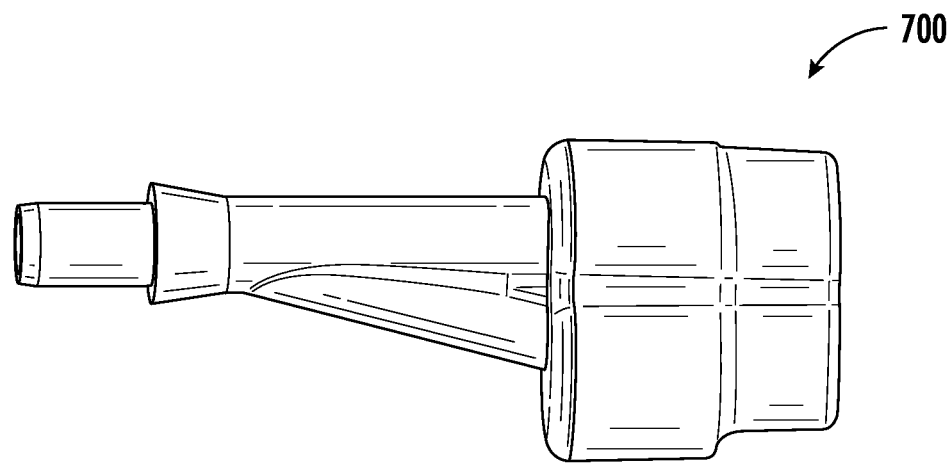
FIGS. 7A-7B illustrate a perspective and cross-sectional view, respectively, of a coaxial split connector as an adaptor for a tubing assembly, according to an embodiment of the present disclosure.
Figure 7B:
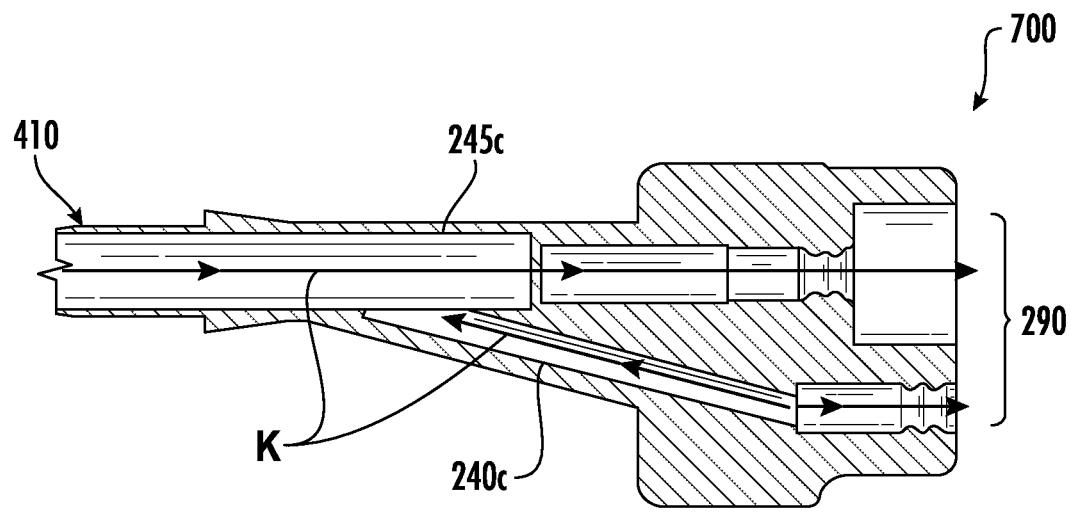

In accordance with one or more embodiments of the present disclosure, the various portions of supply tubing may include an end opposing the manifold end. In accordance with one or more aspects of the present disclosure, the opposing end of the tubing such as the opposing ends of the irrigation supply tubing, the lens wash supply tubing, the gas supply tubing, and the alternative gas supply tubing may be capped, closed, sealed, or the like (such terms being used interchangeably without intent to limit or otherwise convey different meaning or intent) during manufacturing to create a permanent sealed assembly. Thereafter, in use, the opposing ends of the tubing may be punctured by, for example, a piercing or penetrating member. For example, in one embodiment, the piercing or penetrating member may be in the form of one or more of a one-way valve, connector, coaxial split connector, or the like coupled to the opposing end of the tubing. For example, in one embodiment and as schematically illustrated in FIGS. 7A 7B (described further below), a coaxial split connector 700 may be arranged and configured to pierce or penetrate the sealed portion when the coaxial split connector is coupled to the opposing end of the tubing. The capped or sealed portion may be configured along any portion of the tubing. For example, in one embodiment, a capped or sealed portion may be positioned adjacent to an end portion of the opposing end of the tubing, or at some point inside of the tubing.

Referring to FIGS. 7A-7B, in one embodiment, an adapter may be in the form of a coaxial split connector 700 coupled to the tubing, either directly or indirectly. For example, in connection with the illustrated embodiment, a coaxial split connector 700 may be coupled, directly or indirectly, to the endoscope end of the coaxial tubing (e.g., tubing 410 of FIG. 4, and the lens wash supply tubing 245c, 645c and the gas supply tubing 240c, 640c of FIGS. 2, 6A-6B), so that the coaxial portions of tubing may be coupled to the endoscope via the gas/lens wash connection 290. In use, the coaxial split connector 700 may allow for flow to transition between a coaxial arrangement and a side-by-side arrangement with flow path K shown in FIG. 7B.

Figure 8:
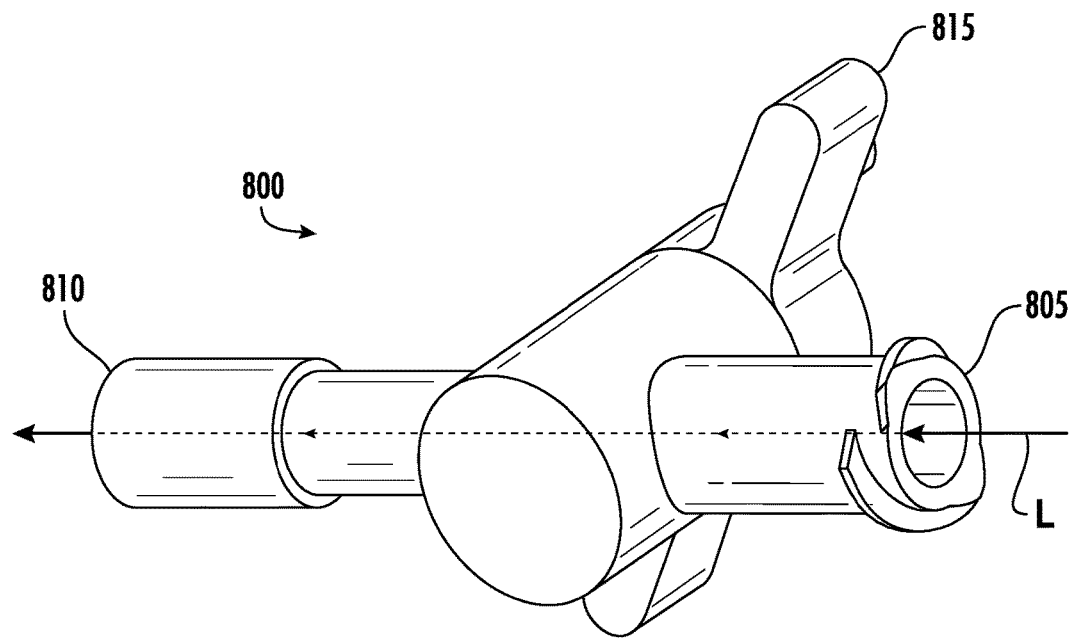
FIG. 8 illustrates a perspective view of a stop-cock adaptor for a tubing assembly, according to an embodiment of the present disclosure.

Referring to FIG. 8, in some embodiments, an adapter may be in the form of, for example, an adjustable connector. For example, in one embodiment, as illustrated, an adapter may be in the form of a stop-cock adaptor 800 having an inlet opening 805, outlet opening 810, and switch 815 In use, the stop-cock adaptor may be coupled, directly or indirectly, to the opposing end of one or more of the tubing. For example, the alternative gas supply tubing 515 may include a stop-cock adaptor. In use, a stop-cock adaptor may be manipulated by a user from a closed position to an opened position. Thus arranged, the user can enable fluid flow through the respective tubing by manipulating the stop-cock adaptor between the closed and opened positions. For example, the user may move the stop-cock adaptor from the closed position to the opened position to enable an alternate gas supply (e.g., $CO_2$) to flow from an alternate gas source into manifold 502, 602 via the alternative gas supply tubing 515.

Figure 9:
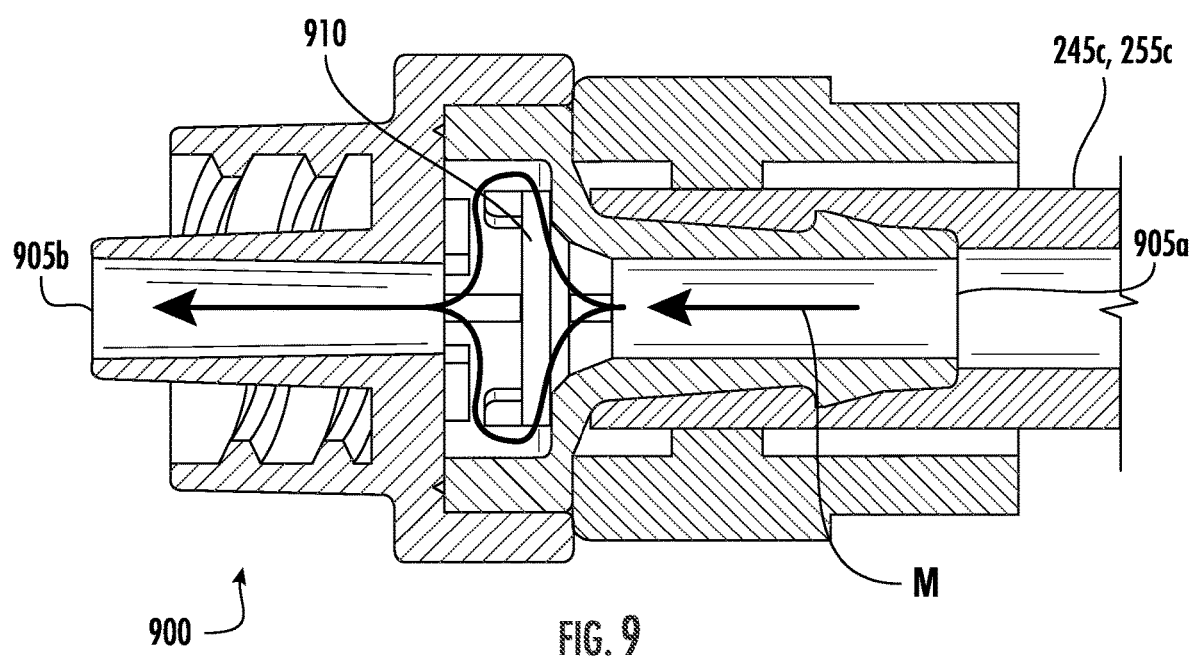
FIG. 9 illustrates a cross-sectional view of a one-way valve as a fitting for a tubing assembly, according to an embodiment of the present disclosure.

Referring to FIG. 9, in some embodiments, each or any of the portions of tubing may include, for example, a one-way valve 900 at an opposing end thereof. In use, the one-way valve 900 comprises inlet 905a, outlet 905b, and one-way valve insert 910. FIG. 9 illustrate flow path M, passing into valve 900 through inlet 905a, around valve insert 910 and through outlet 905b. Backflow of fluid in the direction of inlet 905a is prevented by valve insert 910. That is, incorporation of a one-way valve 900 into any or each of the opposing ends of the portions of gas supply, irrigation supply. lens wash supply, or alternate gas supply tubing ensures that the tubes are sealed to the surrounding environment and the fluid reservoir 570 remains sterile, until operation, or during a prolonged period of operation (e.g., 24-hour period). In some embodiments, a one-way valve, such as valve 900, may be arranged and configured with a penetrating member to puncture or pierce a seal or member in one of the various portions of tubing when the one-way valves are coupled thereto.

Referring to FIGS. 10A-11C, various embodiments and aspects of an endoscope system 1000, 1100 are disclosed. In accordance with one or more aspects of the present invention, the endoscope systems 1000, 1100 may be substantially similar to endoscope and tubing systems, or components thereof, disclosed above in connection with FIGS. 1-9 except as outlined herein. Similarly, in accordance with one or more aspects of the present invention, the endoscope system 1000, or components thereof, may be substantially similar to the endoscope system 1100, or components thereof, disclosed in connection with FIGS. 11A-11C except as outlined herein. Additionally, in accordance with one or more aspects of the present invention, the endoscope system 1100, or components thereof, may be substantially similar to the endoscope system 1000, or components thereof, disclosed in connection with FIGS. 10A-10F except as outlined herein. Thus for the sake of brevity, detailed description of similar elements may be omitted herefrom.

Figure 10A:
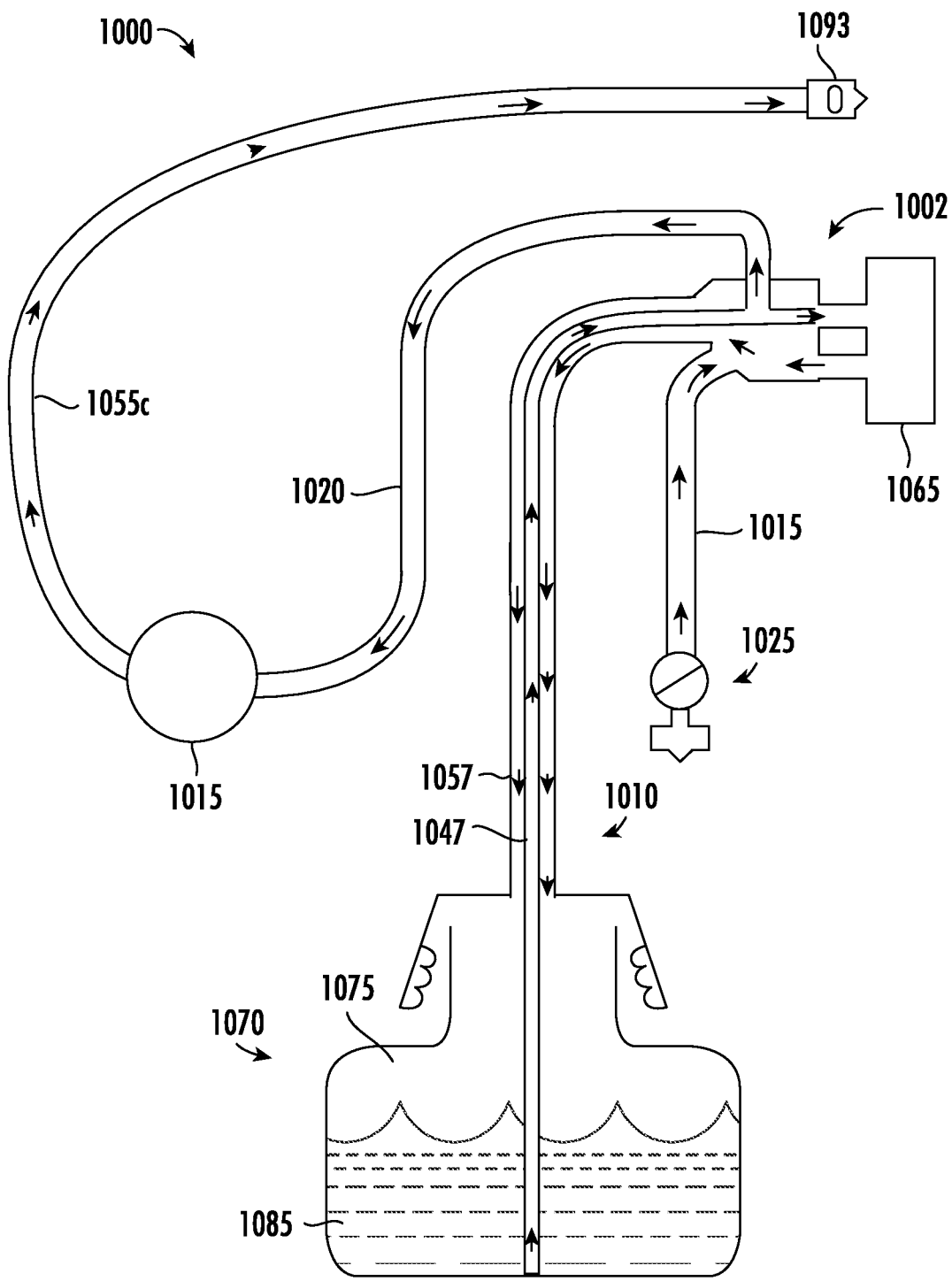
FIGS. 10A-10F illustrate various aspects of an endoscope system comprising a manifold assembly, according to an embodiment of the present disclosure.

FIGS. 10A-10F illustrate various aspects of an endoscope system 1000 comprising a manifold assembly 1002, according to an embodiment of the present disclosure. In FIG. 10A, the endoscope system 1000 includes a tubing assembly 1001 with the manifold assembly 1002 and a connector portion 1065. As will be appreciated, the connector portion 1065 may be the same or similar to connector portion 265. Accordingly, the connector portion 1065 may couple the tubing assembly 1001 to one or more portions of the endoscope system 1000 not illustrated in FIG. 10A (see e.g., FIG. 5A).

Referring to FIG. 10A, the tubing assembly 1001 may include reservoir 1070, coaxial tubing 1010, manifold assembly 1002, alternative gas supply tubing 1015, alternative gas connection 1025, upstream irrigation supply tubing 1020, irrigation pump 1017, downstream irrigation supply tubing 1055c, and irrigation connection 1093. The coaxial tubing 1010 may include an outer tube (e.g., gas supply tubing 1057) and an inner tube (e.g., liquid supply tubing 1047). The reservoir 1070 may include a fluid 1085 with a gap 1075 above the fluid.

In various embodiments, a gas may be introduced into the gap 1075, such as via gas supply tubing 1057, to pressurize the reservoir 1070 and cause the fluid 1085 to flow out of the reservoir 1070 via the liquid supply tubing 1047. In various such embodiments, the gas may be introduced into the gap from a source coupled to connector portion 1065 (e.g., air pump 215) or from a source coupled to the alternative gas connection 1025 (e.g., a bottle of carbon dioxide). Alternatively, or additionally, irrigation pump 1017 may be utilized to draw fluid 1085 out of the reservoir 1070. In many embodiments, introduction of a gas into gap 1075 may be utilized to remove fluid 1085 from the reservoir 1070 for lens wash functionality while irrigation pump 1017 may be utilized to remove fluid 1085 from the reservoir 1070 for irrigation functionality. In some embodiments, the upstream irrigation supply tubing 1020 may be more rigid or robust than the downstream irrigation supply tubing 1055c. For example, upstream irrigation supply tubing may be more resistant to collapse than the downstream irrigation supply tubing.

Figure 10B:
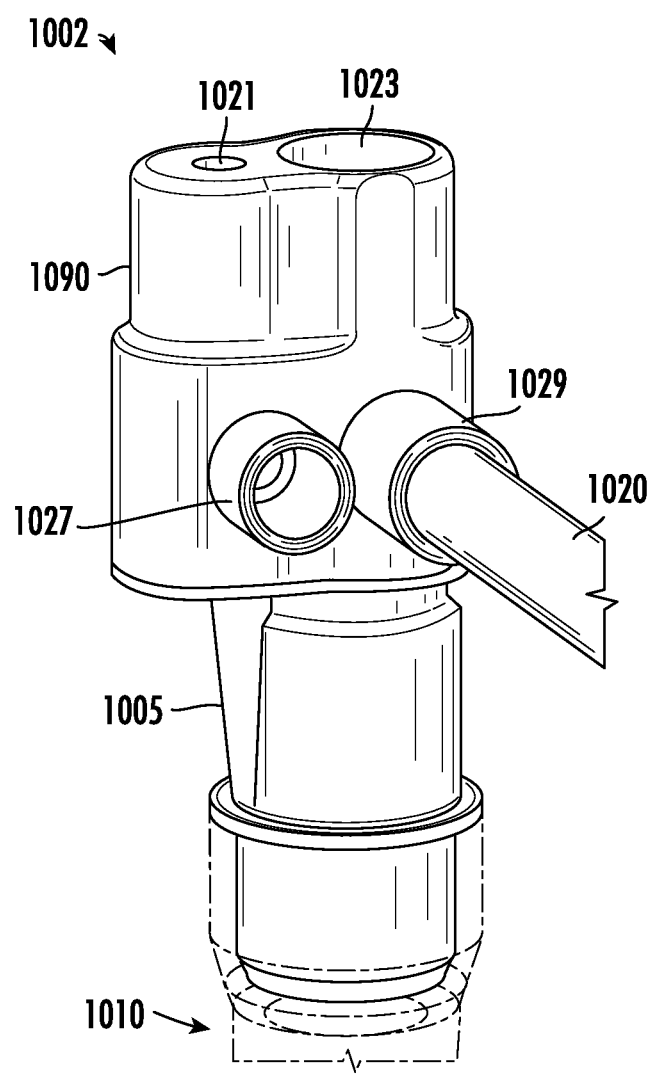

Referring to FIG. 10B, the manifold assembly 1002 is shown coupled to coaxial tubing 1010 and upstream irrigation supply tubing 1020. Manifold assembly 1002 may include a gas/lens wash connection 1090 and a fluid manifold 1005. The gas/lens wash connection 1090 may couple with connector portion 1065 of the endoscope system 1000. As will be discussed in more detail below, the fluid manifold 1005 may function to separate, or combine, inner and outer tubes of coaxial tubing 1010 while preventing fluid communication between the inner and outer tubes. For example, fluid manifold 1005 may route fluid from the liquid supply tubing 1047 of coaxial tubing 1010 into upstream irrigation supply tubing 1020 while preventing fluid communication between the gas supply tubing 1057 of coaxial tubing 1010 and the upstream irrigation supply tubing 1020. In various embodiments, the fluid manifold 1005 may be made of a rigid material (e.g., a metal, a high density polyurethane (HDPE), and the like) and the gas/lens wash connection 1090 may be made of a flexible material (e.g., a polymer and the like). As shown in additional detail below in FIG. 10E, the gas/lens wash connection 1090 may fit over and be assembled onto a portion of the fluid manifold 1005.

Figure 10C:
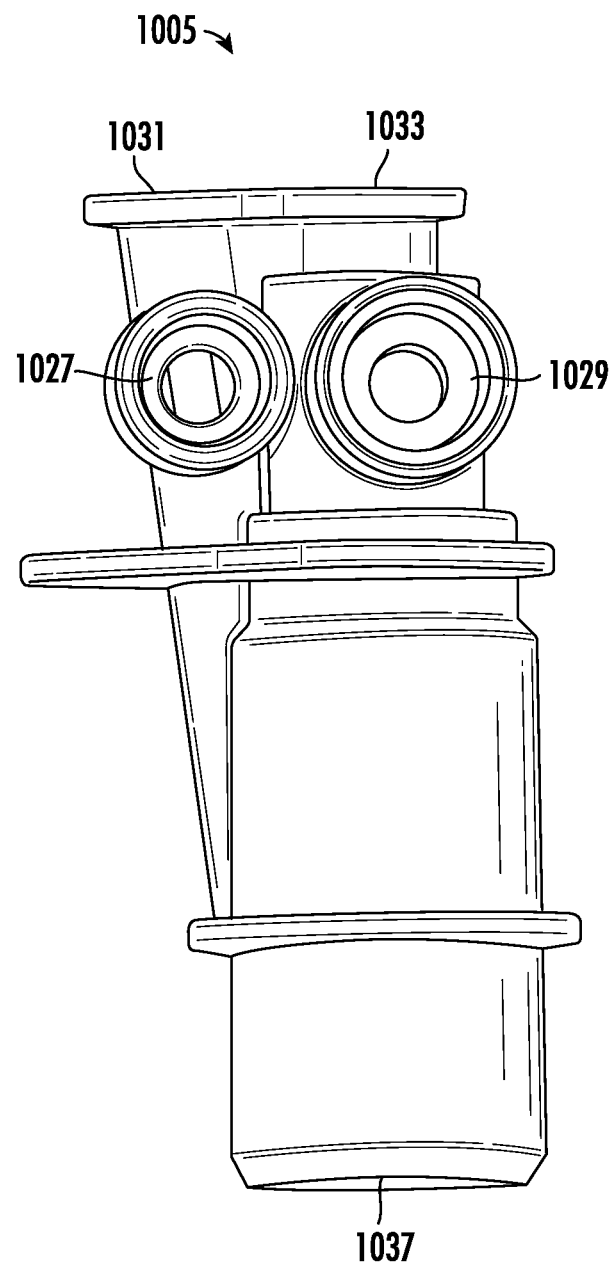

As shown in FIG. 10C, the fluid manifold 1005 may include a gas umbilicus port 1031, a lens wash umbilicus port 1033, an alternative gas supply port 1027, an irrigation supply port 1029, and a coaxial tubing port 1037. In various embodiments, the gas umbilicus port 1031 may extend from the fluid manifold 1005 at an obtuse angle with respect to the coaxial tubing port 1037. In some embodiments, the alternative gas supply port 1027 and/or the irrigation supply port 1029 may extend from the fluid manifold 1005 at a perpendicular angle with respect to one or more of the gas umbilicus port 1031, the lens wash umbilicus port 1033, and the coaxial tubing port 1037.

Figure 10D:
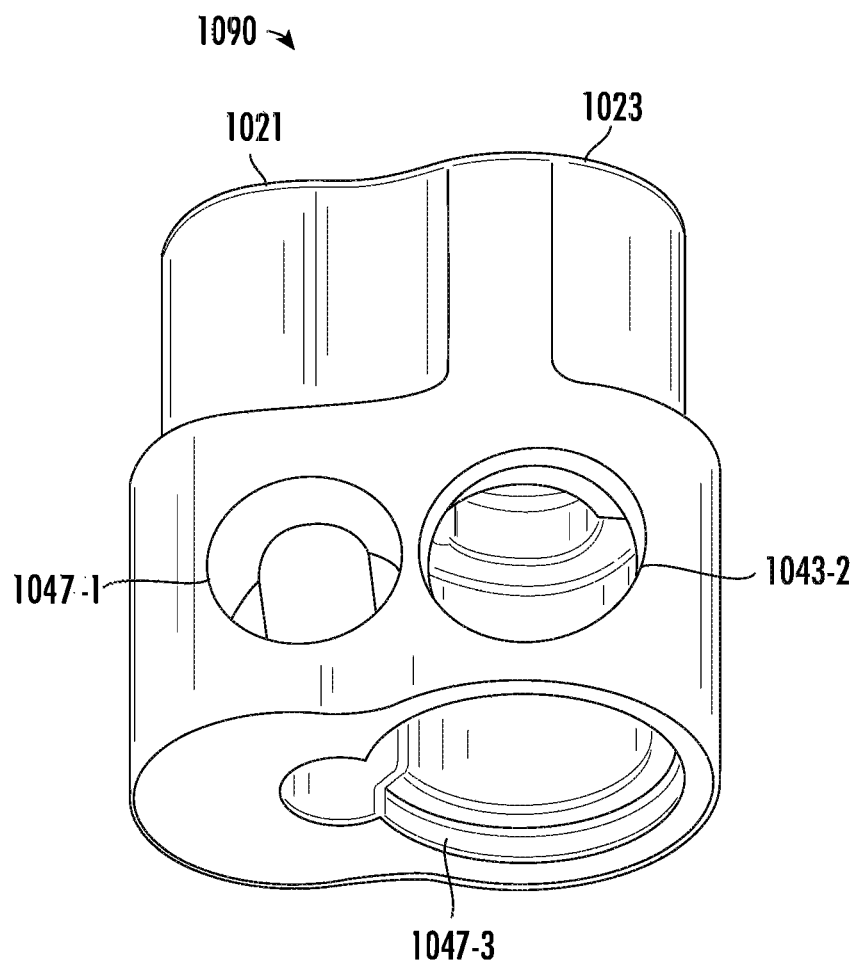

As shown in FIG. 10D, the gas/lens wash connection 1090 may include a gas connector 1021, a lens wash connector 1023, and openings 1047-1, 1047-2, 1047-3. When assembled onto fluid manifold 1005, the alternative gas supply port 1027 may extend out of the first opening 1047-1, the irrigation supply port 1029 may extend out of the second opening 1047-2, and the coaxial tubing port 1037 may extend out of the third opening 1047-3. As previously mentioned, the gas/lens wash connection 1090 may be made from a flexible material. Accordingly, the gas/lens wash connection 1090 may be stretched over portions of the fluid manifold 1005 to assemble the gas/lens wash connection 1090 onto the fluid manifold 1005.

Figure 10E:
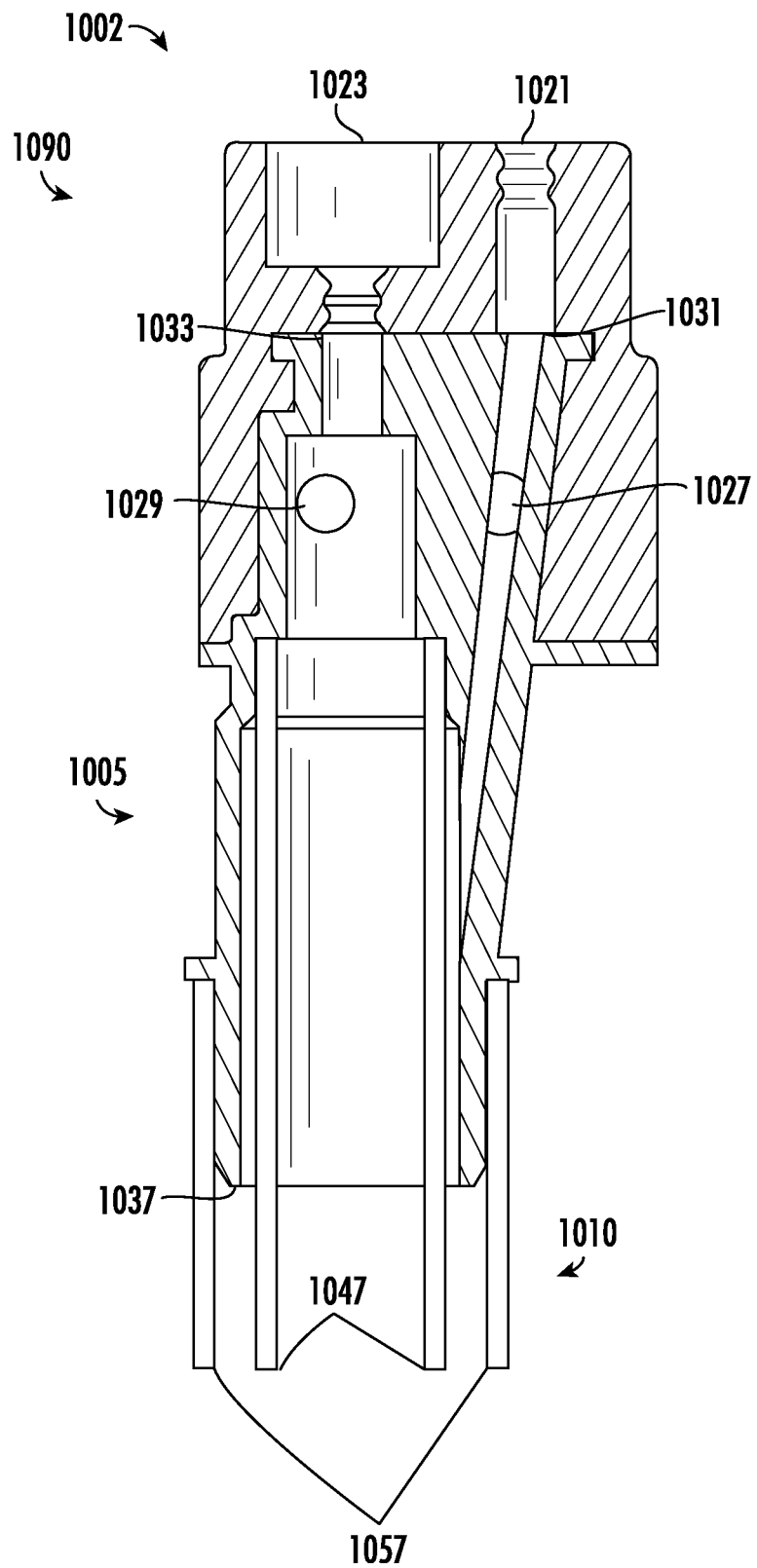

FIG. 10E illustrates a cross-sectional view of the manifold assembly 1002 with coaxial tubing 1010 connected. When assembled, the lens wash connector 1023 of gas/lens wash connection 1090 may be aligned with and in fluid connection with lens wash umbilicus port 1033 and the gas connector 1021 of gas/lens wash connection 1090 may be aligned with and in fluid communication with gas umbilicus port 1031. As shown in the illustrated embodiment, in various embodiments, the lens wash connector 1023 and/or the gas connector 1021 of the gas/lens wash connection 1090 may include one or more features (e.g., changes in diameter, shapes, steps, and the like) to facilitate reliable and robust (e.g., leak-free) connections with the connector portion 1065.

Referring to the connection of the coaxial tubing 1010 to the fluid manifold 1005 shown in FIG. 10E, the inner tube (liquid supply tubing 1047) may extend into an interior portion of the fluid manifold 1005 and the outer tube (gas supply tubing 1057) may extend around (or surround) an exterior portion of the fluid manifold 1005. Further, the lumen of the liquid supply tubing 1047 may be in fluid communication with the lens wash connector 1023, the lens wash umbilicus port 1033, and the irrigation supply port 1029. The lumen of the gas supply tubing 1057 may be in fluid communication with the alternative gas supply port 1027, the gas umbilicus port 1031, and the gas connector 1021.

Figure 10F:
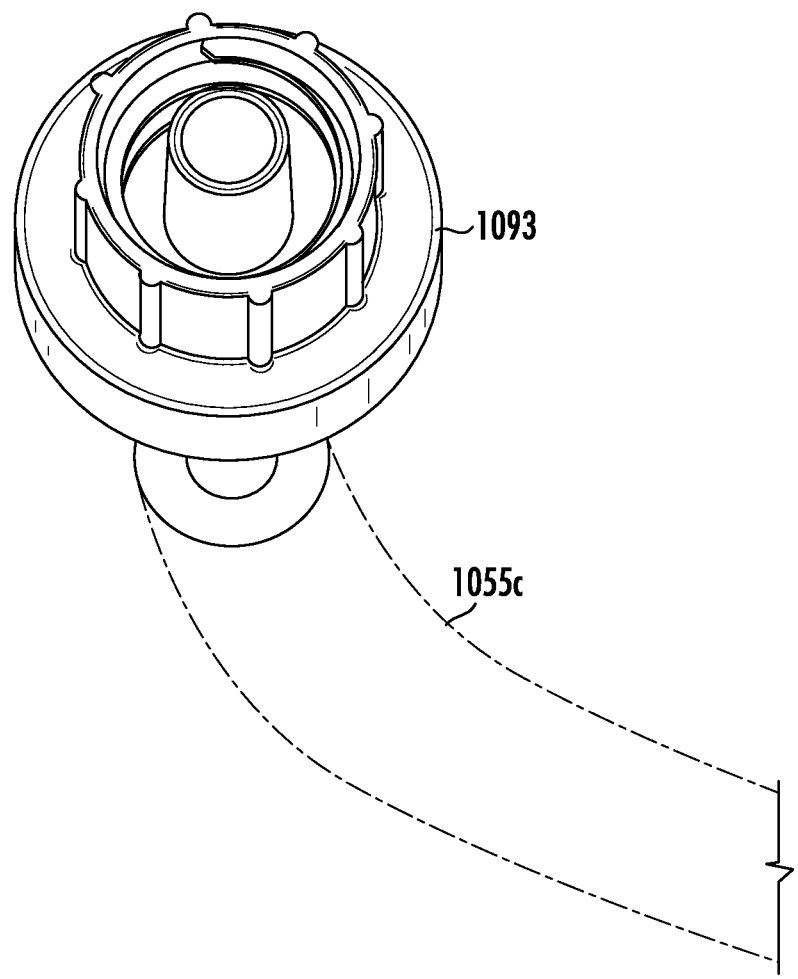

FIG. 10F illustrates a detailed view of the irrigation connection 1093 and downstream irrigation supply tubing 1055c. In many embodiments, the irrigation connection 1093 may couple to connector portion 1065. In some embodiments, irrigation connection 1093 may include one or more of a luer fitting, a check valve, and an on/off valve. More generally, one or more connection described herein may include one or more of a luer fitting, a check valve, and an on/off valve. For example, alternative gas connection 1025 may include an on/off valve and a luer connection. In various embodiments, irrigation connection 1093 may be a threaded connection.

Figure 11A:
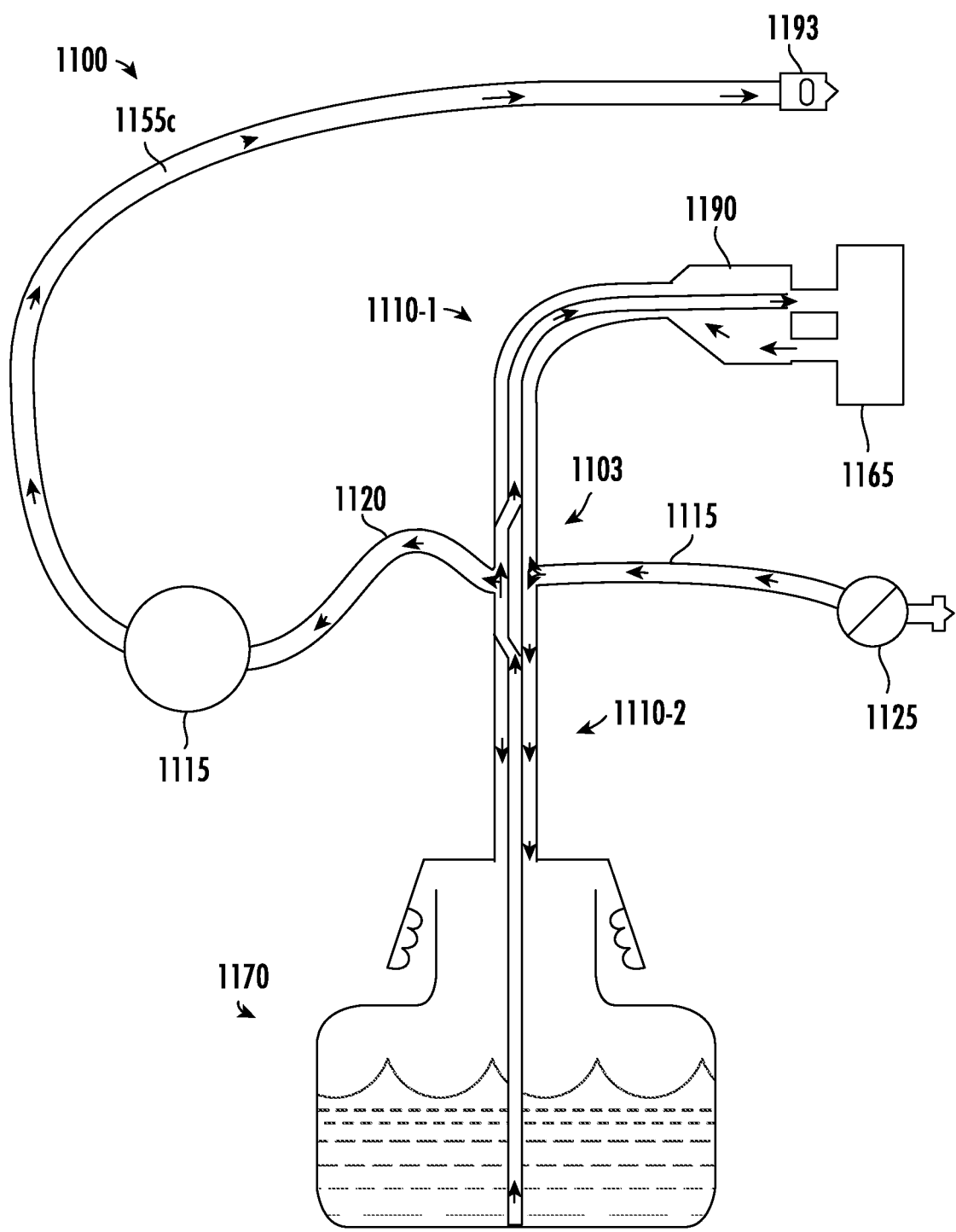
FIGS. 11A-11C illustrate various aspects of an endoscope system comprising a split manifold, according to an embodiment of the present disclosure.
Figure 11B:
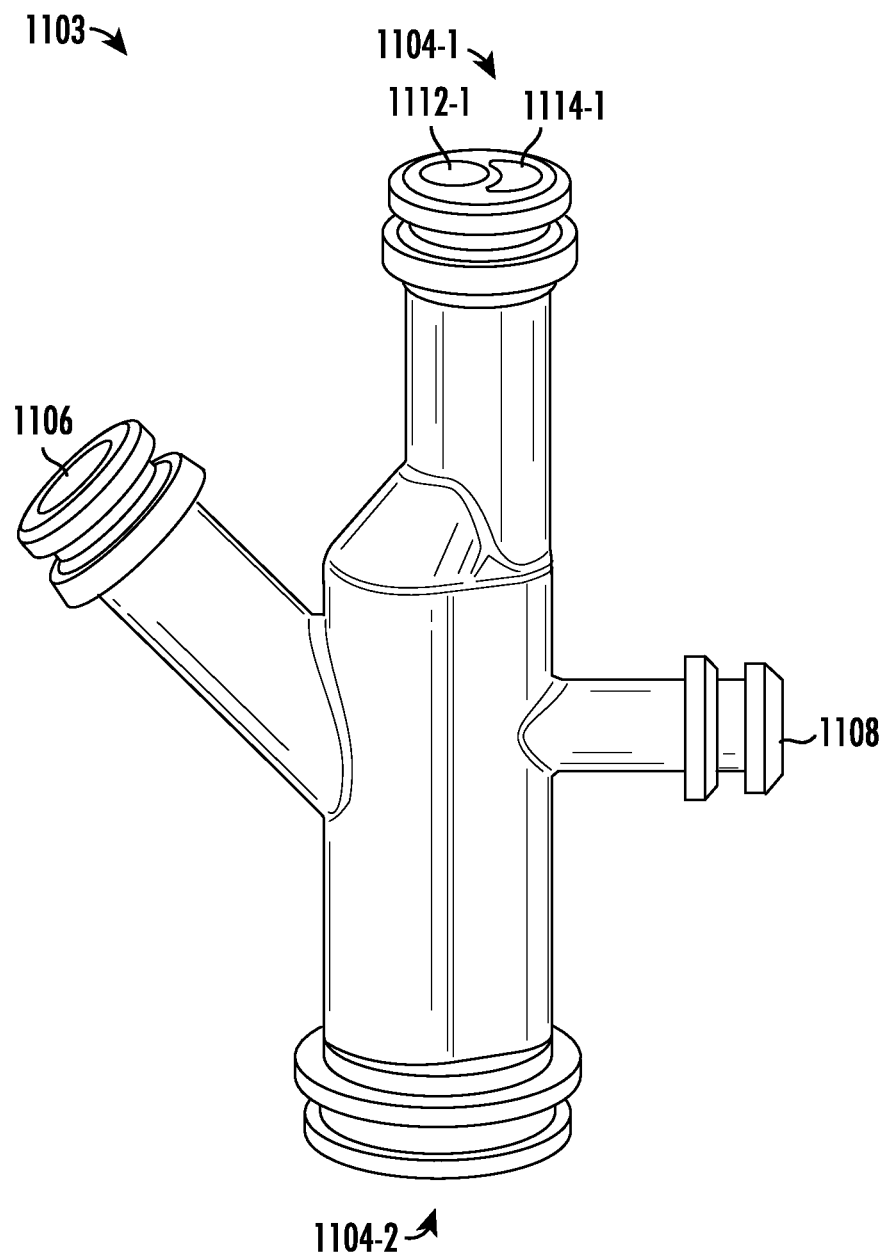
Figure 11C:
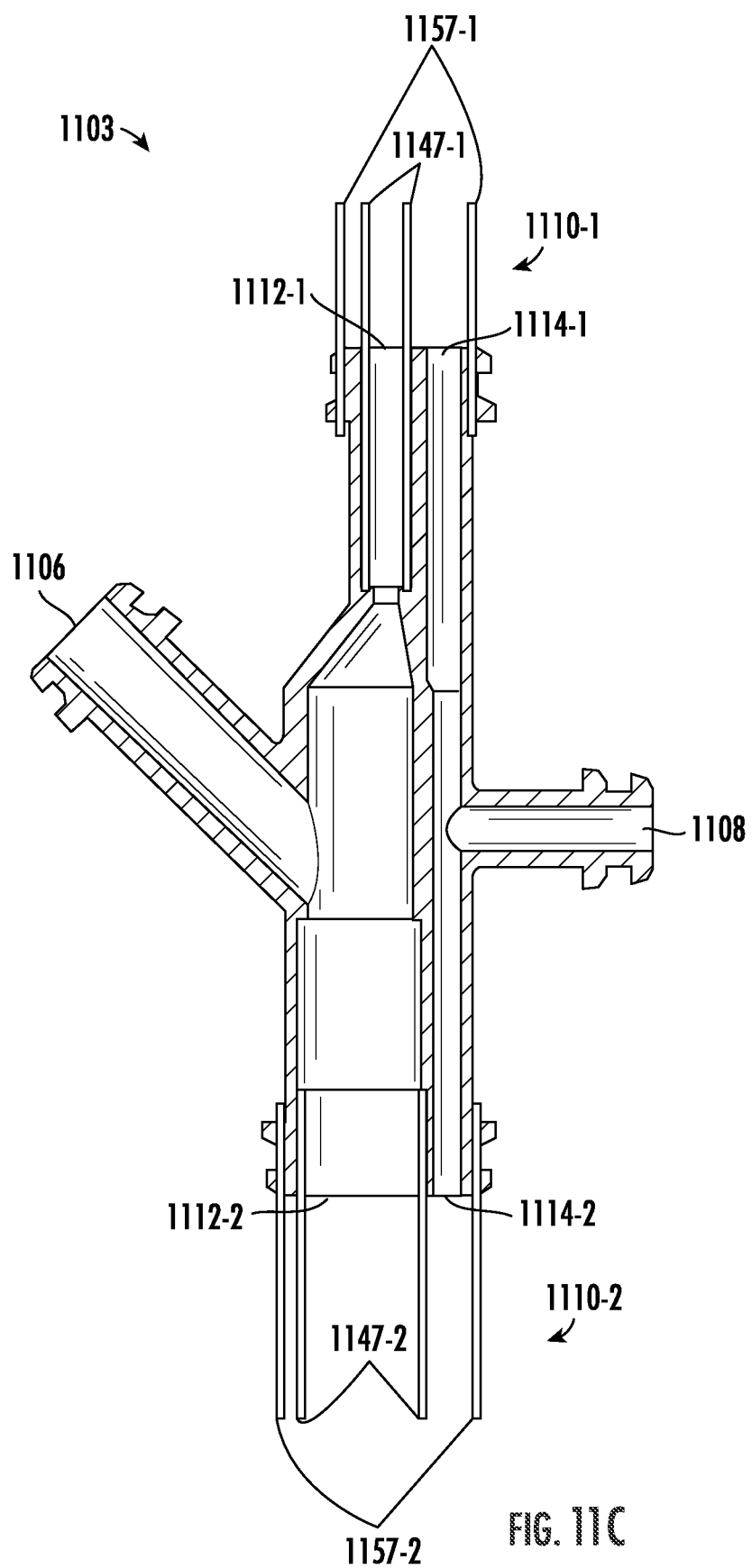

FIGS. 11A-11C illustrate various aspects of an endoscope system 1100 comprising a split manifold 1103, according to an embodiment of the present disclosure. In FIG. 11A, the endoscope system 1100 includes a tubing assembly 1101 with the split manifold 1103 and a connector portion 1165. As will be appreciated, the connector portion 1165 may be the same or similar to connector portion 265. Accordingly, the connector portion 1165 may couple the tubing assembly 1101 to one or more portions of the endoscope system 1100 not illustrated in FIG. 11A (see e.g., FIG. 5A).

Referring to FIG. 11A, the tubing assembly 1101 may include split manifold 1103, first coaxial tubing 1110-1, gas/lens wash connection 1190, second coaxial tubing 1110-2, reservoir 1170, alternative gas supply tubing 1115, alternative gas connection 1125, upstream irrigation supply tubing 1120, irrigation pump 1117, downstream irrigation supply tubing 1155c, and irrigation connection 1193. Coaxial tubing 1110-1, 1110-2 may each include an inner tube and an outer tube. In many embodiments, the outer tube may be utilized to convey gases and the inner tube may be utilized to convey liquids. The reservoir 1170 may include a fluid with a gap above the fluid. In some embodiments, gas/lens wash connection 1190 may be the same or similar to manifold assembly 1002 without the alternative gas supply port 1027 and without the irrigation supply port 1029.

In endoscope system 1100, similar to system 1000, a gas may be introduced into the gap, such as via the outer tube of coaxial tubing 1110-2, to pressurize the reservoir 1170 and cause fluid to flow out of the reservoir 1170 via the inner tube of coaxial tubing 1110-2. In various such embodiments, the gas may be introduced into the gap from a source coupled to connector portion 1165 (e.g., air pump 215) or from a source coupled to the alternative gas connection 1125 (e.g., a bottle of carbon dioxide). Alternatively, or additionally, irrigation pump 1117 may be utilized to draw fluid out of the reservoir 1170. In many embodiments, introduction of a gas into gap may be utilized to remove fluid from the reservoir 1170 for lens wash functionality while irrigation pump 1117 may be utilized to remove fluid from the reservoir 1170 for irrigation functionality. In some embodiments, the upstream irrigation supply tubing 1120 may be more rigid or robust than the downstream irrigation supply tubing 1155c. For example, upstream irrigation supply tubing may be more resistant to collapse than the downstream irrigation supply tubing.

Referring to FIG. 11B, the split manifold 1103 may include a first coaxial tubing port 1104-1, an irrigation supply port 1106, an alternative gas supply port 1108, and a second coaxial tubing port 1104-2. The first coaxial tubing port 1104-1 may include a first liquid port 1112-1 and a first gas port 1114-1. Similarly, as shown in FIG. 11C, the second coaxial tubing port 1104-2 may include a second liquid port 1112-2 and a second gas port 1114-2. In various embodiments, the irrigation supply port 1106 may extend from the split manifold 1103 at an obtuse angle with respect to the coaxial tubing port 1104-2 (and/or an acute angle with respect to the coaxial tubing port 1104-1). In some embodiments, the alternative gas supply port 1108 may extend from the split manifold 1103 at a perpendicular angle with respect to one or more of the coaxial tubing ports 1104-1, 1104-2. In various embodiments, the split manifold 1103 may be made of a rigid material (e.g., a metal, a high density polyurethane (HDPE), and the like).

FIG. 11C illustrates the split manifold 1103 coupled to the first coaxial tubing 1110-1 at coaxial tubing port 1104-1 and coupled to the second coaxial tubing 1110-2 at coaxial tubing port 1104-2. As will be discussed in more detail below, the split manifold 1103 may function to separate, or combine, inner and outer tubes of the first coaxial tubing 1110-1 and the second coaxial tubing 1110-2 while preventing fluid communication between the inner and outer tubes. For example, split manifold 1103 may route fluid from the liquid supply tubing 1147-2 of coaxial tubing 1110-2 into upstream irrigation supply tubing 1120 while preventing fluid communication between the gas supply tubing 1157-1 of coaxial tubing 1110-1 and the upstream irrigation supply tubing 1120, the gas supply tubing 1157-2 of coaxial tubing 1110-2 and the upstream irrigation supply tubing 1120, and the alternative gas supply port 1108 and the upstream irrigation supply tubing 1120. In other words, when coupled to coaxial tubes 1110-1, 1110-2, split manifold 1103 may place liquid port 1112-1 in fluid communication with irrigation supply port 1106 and liquid port 1112-2 and place gas port 1114-1 in fluid communication with alternative gas supply port 1108 and gas port 1114-2.

Referring to the connection of the coaxial tubes 1110-1, 1110-2 to the split manifold 1103 shown in FIG. 11C, the inner tubes (liquid supply tubes 1147-1, 1147-2) may extend into an interior portion of the split manifold 1103 and the outer tubes (gas supply tubes 1157-1, 1157-2) may extend around (or surround) an exterior portion of the split manifold 1103. Further, the lumens of the liquid supply tubes 1147-1, 1147-2 may be in fluid communication with the irrigation supply port 1106 and the lumens of the gas supply tubes 1157-1, 1157-2 may be in fluid communication with the alternative gas supply port 1108.

Figure 12:
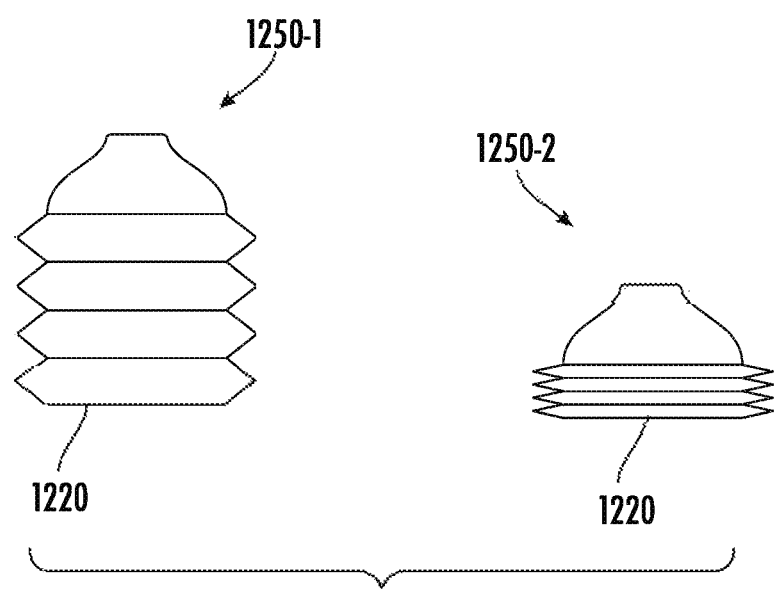
FIG. 12 illustrates a reservoir in first and second states, according to an embodiment of the present disclosure.

FIG. 12 illustrates a reservoir 1220 in a first and second states, according to an embodiment of the present disclosure. More specifically, the first state includes reservoir 1220 in an expanded state 1250-1 and the second state includes reservoir 1220 in a collapsed state 1250-2. In various embodiments, collapsibility may reduce storage space requirements. Further, collapsibility may reduce storage space requirements without sacrificing fluid holding capacity. In some embodiments, the curved design of the necking portion may reduce, or prevent, backflow into gas tubes connected thereto.

More generally, in accordance with one or more aspects of the present invention, various fluid reservoirs disclosed hereby may be arranged in a non-rigid configuration (e.g., the fluid reservoir 570 may be arranged and configured as a compressible reservoir). For example, the reservoir 570 may be in the form of a pouch, a bag, or other soft fluid container similar to a saline style pouch (such terms being used interchangeably without intent to limit or otherwise convey different meaning or intent). Thus arranged, the non-rigid reservoir 570 or reservoir 1220 may be referred to as a pouch herein. In accordance with this embodiment, a pouch as fluid reservoir 570 may be manufactured from a suitable uniform material including, for example, plastics, elastomers, or any other suitable material now known or hereafter developed.

In use, the valves, connectors, adapters, or the like, such as the examples of FIGS. 5A-12 may be arranged and configured to couple to the tubing via any suitable mechanism or method now known or hereafter developed. For example, the valves, connectors, or adapters may be press-fitted onto the tubes. Alternatively, anchoring methods, such as luer fittings, threaded connections, or the like, may be utilized. In either event, once coupled to the tubing, the valves, connectors, or adapters are arranged and configured to create a seal with the tubing to prevent leaks at the puncture point.

As will be appreciated, the portions of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

In various embodiments, a tubing method for distributing fluid during an endoscopic procedure, according to the present disclosure, may comprise connecting a portion of gas supply tubing and a portion of lens wash supply tubing in fluid communication between an endoscope and a tubing manifold and connecting a portion of gas supply tubing and a portion of lens wash supply tubing in fluid communication between the tubing manifold and a fluid reservoir. A gas may be supplied to the fluid reservoir through the gas supply tubing between the endoscope and the manifold and between the manifold and the fluid reservoir. A lens wash fluid from the fluid reservoir may be supplied through the lens wash supply tubing between the fluid reservoir and the manifold and between the manifold and the endoscope.

In some embodiments, the method may further comprise connecting a portion of irrigation supply tubing in fluid communication between the endoscope and the manifold, between the manifold and the fluid reservoir, or both. An irrigation fluid from the fluid reservoir may be supplied through the irrigation supply tubing between the fluid reservoir and the manifold and between the manifold and the endoscope. In some embodiments, the portion of lens wash supply tubing and the portion of irrigation supply tubing between the fluid reservoir and the manifold are the same portion of tubing. A flow of fluid may be supplied from the fluid reservoir to the manifold for irrigation use, lens wash use, or both, through separate portions or through the same portions of lens wash supply tubing and irrigation supply tubing.

In some embodiments, the method may further comprise connecting a portion of an alternate gas supply tubing in fluid communication between an alternate gas source and the manifold, between the manifold and the fluid reservoir, between the manifold and the endoscope, or combinations thereof. In some embodiments, the gas supply tubing is used to supply a gas (e.g., air) from the endoscope through the manifold to the fluid reservoir, while the alternate gas supply tubing is closed off to flow from the alternate gas source. In other embodiments, the alternate gas supply tubing is used to supply an alternate gas (e.g., $CO_2$) from the alternate gas source through the manifold to the fluid reservoir, while the gas supply tubing is closed off to flow from the endoscope (e.g., by turning off the pump in the video processing unit). In either arrangement, the gas supply or alternate gas supply pressurizes the fluid reservoir forcing fluid through the manifold and the portion of lens wash supply tubing for use through the endoscope during a procedure as a lens wash fluid. Simultaneously, or at different times, the irrigation pump may be activated (e.g., via a foot switch) to draw fluid from the fluid reservoir through the manifold and the portion of irrigation supply tubing for use though the endoscope during as an irrigation fluid.

The flow rate and/or volume of fluid supplied from the fluid reservoir through the manifold for use as irrigation fluid may be controlled (e.g., by an irrigation pump) to be different compared to use as lens wash fluid, even though the fluid is being sourced from the same fluid reservoir, since the lens wash flow may be controlled by varying the gas supply. The gas supply pressurizing the fluid reservoir may also be calibrated to maintain equilibrium in the fluid reservoir as fluid is withdrawn for use as irrigation and/or lens wash, even if both functions are performed simultaneously.

When gas supply is desired for use through the endoscope during a procedure, e.g., as an insufflating gas, the gas/lens wash valve may be actuated to redirect the gas supply or alternate gas supply from the fluid reservoir to the endoscope.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. A tubing assembly arranged and configured to couple to an endoscope for distributing fluid between the endoscope and a fluid reservoir during an endoscopic procedure, the assembly comprising:
    a tubing manifold, comprising:
        a gas channel having a gas opening, an alternate gas opening, and a combined gas/alternate gas opening, and
        a liquid channel having an irrigation opening, a lens wash opening, and a combined lens wash/irrigation opening;
    a cap configured to be removably attached to the fluid reservoir;
    gas supply tubing, a portion of which is configured for connection in fluid communication between the gas opening of the manifold and the endoscope, and a portion of which is configured for connection in fluid communication between the cap and the combined gas/alternate gas opening of the manifold; and
    alternate gas supply tubing, a portion of which is configured for connection in fluid communication between the alternate gas opening of the manifold and the endoscope, and a portion of which is configured for connection in fluid communication between the cap and the combined gas/alternate gas opening of the manifold;
    lens wash supply tubing, a portion of which is configured for connection in fluid communication between the lens wash opening of the manifold and the endoscope, a portion of which is configured for connection in fluid communication between the fluid reservoir and the combined lens wash/irrigation opening of the manifold; and
    irrigation supply tubing, a portion of which is configured for connection in fluid communication between the irrigation opening of the manifold and the endoscope, a portion of which is configured for connection in fluid communication between the fluid reservoir and the combined lens wash/irrigation opening of the manifold.

2. The assembly according to claim 1, wherein the portions of lens wash supply tubing and irrigation supply tubing between the fluid reservoir and the combined lens wash/irrigation opening of the manifold are the same portion of tubing.

3. The assembly according to claim 2, wherein the same portion of lens wash supply tubing and irrigation supply tubing between the combined lens wash/irrigation opening of the manifold and the fluid reservoir is arranged coaxially within the portion of gas supply tubing between the combined gas/alternate gas opening of the manifold and the cap.

4. The assembly according to claim 1, wherein the portion of lens wash supply tubing between the endoscope and the lens wash opening of the manifold is arranged coaxially within the portion of gas supply tubing between the endoscope and the gas opening of the manifold.

5. The assembly according to claim 1, wherein the portions of gas supply tubing and alternate gas supply tubing between the combined gas/alternate gas opening of the manifold and the endoscope are the same portion of tubing, and the portions of gas supply tubing and alternate gas supply tubing between the combined gas/alternate gas opening of the manifold and the cap are the same portion of tubing.

6. The assembly according to claim 1, wherein the portion of irrigation supply tubing between the irrigation opening of the manifold and the endoscope is selectively connectable to the manifold, the portion of tubing further comprising a penetrating member disposed on a manifold end thereof.

7. The assembly according to claim 6, the irrigation opening comprising a breakable seal puncturable by the penetrating member of the portion of irrigation supply tubing when selected to be connectable thereto.

8. A tubing method for distributing fluid during an endoscopic procedure, the method comprising:
    connecting a portion of gas supply tubing and a portion of lens wash supply tubing in fluid communication between an endoscope and a tubing manifold, the tubing manifold comprising:
        a gas channel having a gas opening, an alternate gas opening, and a combined gas/alternate gas opening, and
        a liquid channel having an irrigation opening, a lens wash opening, and a combined lens wash/irrigation opening;
    connecting a portion of gas supply tubing and a portion of lens wash supply tubing in fluid communication between the tubing manifold and a fluid reservoir;
    supplying gas to the fluid reservoir through the portions of gas supply tubing between the endoscope and the manifold and between the manifold and the fluid reservoir; and
    supplying lens wash liquid from the fluid reservoir through the portions of lens wash supply tubing between the fluid reservoir and the manifold and between the manifold and the endoscope.

9. The method according to claim 8, further comprising connecting a portion of irrigation supply tubing connected in fluid communication between the endoscope and the manifold, a portion of irrigation supply tubing connected between the manifold and the fluid reservoir, or both.

10. The method according to claim 9, wherein the portions of lens wash supply tubing and irrigation supply tubing between the fluid reservoir and the manifold are the same portion of tubing.

11. The method according to claim 10, further comprising supplying a flow of liquid from the fluid reservoir to the manifold for irrigation use, lens wash use, or both, through the same portion of lens wash supply tubing and irrigation supply tubing.

12. The method according to claim 9, further comprising connecting a portion of alternate gas supply tubing connected in fluid communication between an alternate gas source and the manifold, a portion of alternate gas supply tubing connected between the manifold and the fluid reservoir, a portion of alternate gas supply tubing connected between the manifold and the endoscope, or combinations thereof.

* * * * *